(12) United States Patent
Arenberg et al.

(10) Patent No.: US 6,440,102 B1
(45) Date of Patent: *Aug. 27, 2002

(54) FLUID TRANSFER AND DIAGNOSTIC SYSTEM FOR TREATING THE INNER EAR

(75) Inventors: Irving K. Arenberg; Michael H. Arenberg, both of Englewood, CO (US)

(73) Assignee: Durect Corporation, Cupertino, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/121,460

(22) Filed: Jul. 23, 1998

(51) Int. Cl.[7] .................. A61M 29/00; A61M 31/00; A61F 11/00
(52) U.S. Cl. .................. 604/96.01; 604/97.01; 604/506; 606/108
(58) Field of Search .................. 604/96–98, 104, 604/20–22, 102, 110, 215, 264, 523, 536–537, 506, 508–509, 173–174, 181, 271, 275, 278–279; 606/108–109, 191–192; 607/115–16, 137, 126

(56) References Cited

U.S. PATENT DOCUMENTS

| | | | |
|---|---|---|---|
| 2,642,065 A | 6/1953 | Negri | |
| 3,528,419 A | 9/1970 | Joechle et al. | |
| 4,034,759 A | 7/1977 | Haerr | |
| 4,159,719 A | 7/1979 | Haerr | |
| 4,175,563 A | 11/1979 | Arenberg et al. | |
| 4,244,377 A | 1/1981 | Grams | |
| 4,250,878 A | 2/1981 | Jacobsen et al. | |
| 4,297,748 A | 11/1981 | Moloy | 3/1 |
| 4,320,758 A | 3/1982 | Eckenhoff et al. | |

(List continued on next page.)

FOREIGN PATENT DOCUMENTS

| | | |
|---|---|---|
| EP | 223763 | 5/1987 |
| WO | WO 89/11882 | 12/1989 |
| WO | WO 92/11895 | 7/1992 |

OTHER PUBLICATIONS

Pfleiderer, "The Current Role of Local Intratympanic Gentamicin Therapy in the Mangement of Unilateral Meniere's Disease," *Clin. Otolalaryngol.* vol. 23:34–41 (1998).

Goycoolea, Marcos V., et al., "In Search of Missing Links in Otology. II. Development of an Implantable Middle Ear Drug Delivery System: Initial Studies of Sustained Ampicillin Release for the Treatment of Otitis Media", *Laryngoscope* 101: 727–732 (Jul. 1991).

Goycoolea, Marcos V., et al., "Extended Middle Ear Drug Delivery A New Concept; A New Device", *Acta Otolaryngol.* (Stockh), Suppl. 493:119–126 (1992).

(List continued on next page.)

*Primary Examiner*—Angela D. Sykes
*Assistant Examiner*—P M Bianco
(74) *Attorney, Agent, or Firm*—Carol L. Francis; Paula A. Borden; Bozicevic, Field & Francis, LLP

(57) ABSTRACT

An apparatus for delivering fluid materials into and out of the inner ear via the round window membrane. A fluid transfer conduit is provided which includes one or more passageways therethrough which may have a semipermeable membrane associated therewith to control fluid flow. Attached to the conduit is an inflatable bladder sized for insertion within the round window niche. When inflated, the bladder engages the internal side wall of the niche, thereby securing the bladder and part of the conduit within the niche. The conduit can then transfer fluids to and from the niche and the fluid-permeable round window membrane therein. Bladder inflation may be achieved through one of the passageways within the conduit which can deliver an inflation fluid into the bladder. Also, the conduit may include an elongate conductive diagnostic member for transferring electrical potentials to and from the inner ear.

20 Claims, 6 Drawing Sheets

U.S. PATENT DOCUMENTS

| | | |
|---|---|---|
| 4,419,092 A | 12/1983 | Jacobsen et al. |
| 4,610,686 A | 9/1986 | Ayer et al. |
| 4,757,807 A | 7/1988 | Densert et al. |
| 4,874,368 A | 10/1989 | Miller et al. |
| 4,929,246 A | 5/1990 | Sinofsky |
| 4,968,297 A | 11/1990 | Jacobsen et al. |
| 4,971,076 A | 11/1990 | Densert et al. |
| 4,976,966 A | 12/1990 | Theeuwes et al. |
| 5,035,694 A * | 7/1991 | Kasprzyk et al. ............. 606/27 |
| 5,037,380 A | 8/1991 | Jacobsen et al. |
| 5,219,334 A | 6/1993 | Tsukada |
| 5,236,413 A | 8/1993 | Feiring ........................ 604/21 |
| 5,281,287 A | 1/1994 | Lloyd et al. |
| 5,282,785 A | 2/1994 | Shapland et al. |
| 5,286,254 A | 2/1994 | Shapland et al. |
| 5,304,134 A | 4/1994 | Kraus et al. |
| 5,350,580 A | 9/1994 | Muchow et al. |
| 5,368,037 A | 11/1994 | Eberle et al. |
| 5,419,312 A | 5/1995 | Arenberg et al. |
| 5,421,818 A | 6/1995 | Arenberg |
| 5,474,529 A | 12/1995 | Arenberg |
| 5,476,446 A | 12/1995 | Arenburg |
| 5,797,868 A * | 8/1998 | Leone ......................... 604/21 |
| 5,876,344 A * | 3/1999 | Baker et al. ................ 600/463 |
| 6,045,528 A * | 4/2000 | Arenberg et al. |

OTHER PUBLICATIONS

Kingma, G., et al., "Chronic drug infusion into the scala tympani of the guinea pig cochlea," *Journal of Neuroscience Methods*, 45:127–134 (1992).

House, W.F., "VII. Subarachnoid shunt for drainage of hydrops: a report of 146 cases", *Laryngoscope*, 75:1547–1551 (1965).

Brookler, K.H., et al., "Closed Loop Water Irrigator System", *Otolaryngol. Head Neck Surg.*, 87:364–365 (May–June, 1979).

Kiil, F., "Molecular mechanisms of osmosis", *American Journal of Physiology*, pp. 256–260 (Apr. 1989).

Portmann, M., "Electrophysiological correlates of endolymphatic hypertension and endolymphatic hydrops: an overview of electrocochleography (ECoG)", *Inner Ear Surgery*, Kugler Publications, New York, pp. 241–247 (1991)—I. Arenberg (ed.).

Satoh, Y., et al., "The effects of inline filtration on delivery of gentamicin at various flow rates", *Keio J. Med.*, vol. 41(1):16–20 (Mar. 1992).

Erickson, D., "The Hole Story, Fine–pore membranes remove viruses from biology drugs", *Scientific American*, vol. 267(3), pp. 163–164 (Sep. 1992).

Pillsbury, H.C., III, et al. (ed.), *Operative Challenges in Otolaryngology–Head and Neck Surgery*, Year Book Medical Publishers, Inc., Chicago, 93–101:(1990)—(article therein presented in Chapt. 7 entitled "Nondestructive Surgery for Vertigo" Approach of I. Kaufman Arenberg, et al.).

Pillsbury, H.C., III, et al. (ed.), *Operative Challenges in Otolaryngology–Head and Neck Surgery*, Year Book Medical Publishers, Inc., Chicago, 139–145: (1990)—(article therein presented in Chapt. 10 entitled "Cochlear Implants" Approach of William M. Luxford, et al.).

Co–owned Pending U.S. Patent application Ser. No. 08/874,208 to Arenberg et al. (filed Jun. 13, 1997).

* cited by examiner

FLUID TRANSFER AND DIAGNOSTIC SYSTEM FOR TREATING THE INNER EAR

BACKGROUND OF THE INVENTION

The present invention generally relates to an apparatus and related method for therapeutically treating and/or analyzing conditions of the inner ear. More particularly, the invention involves a multi-functional medical apparatus for use in connection with the middle and inner ear in which the apparatus is capable of (1) delivering therapeutic agents including various medicines in fluid or solid-powder form to internal ear (e.g. inner ear) structures; (2) extracting, withdrawing, or exchanging fluid materials from the inner ear; (3) transferring fluid materials into and out of the inner ear via the round window membrane so that items [1] and [2] can be accomplished; (4) enabling middle and inner ear structures to be electrophysiologically monitored using electrocochleography ("ECoG") procedures; (5) altering the permeability of the round window membrane in the ear for a variety of therapeutic purposes with drugs, chemical agents, or iontophoresis; and (6) creating a discrete sealed or non-sealed "fluid-receiving zone" within the round window niche so that fluid materials can be transferred into and out of the inner ear via the adjacent round window membrane in a controlled and site-specific manner.

In order to treat ear disorders, it may often be necessary to deliver therapeutic agents to various ear tissues in a controlled, safe, and efficient manner. For example, a variety of structures have been developed which are capable of delivering/administering therapeutic agents into the external auditory canal of the outer ear. U.S. Pat. No. 4,034,759 to Haerr discloses a hollow, cylindrical tube manufactured of sponge material (e.g. dehydrated cellulose) which is inserted into the external auditory canal of a patient. When liquid medicines are placed in contact with the tube, it correspondingly expands against the walls of the auditory canal. As a result, accidental removal of the tube is prevented. Furthermore, medicine materials absorbed by the tube are maintained in contact with the walls of the external auditory canal for treatment purposes. Other absorbent devices designed for treatment of the external auditory canal and related tissue structures are disclosed in U.S. Pat. No. 3,528,419 to Joechle, U.S. Pat. No. 4,159,719 to Haerr, and U.S. Pat. No. 2,642,065 to Negri. The Negri patent specifically describes a medicine delivery device with an internally-mounted, frangible medicine container which, when broken, releases liquid medicines into an absorbent member.

However, the delivery of therapeutic agents in a controlled and effective manner is considerably more difficult with respect to tissue structures of the inner ear (e.g. those portions of the ear surrounded by the otic capsule bone and contained within the temporal bone which is the most dense bone tissue in the entire human body). The same situation exists in connection with tissue materials which lead into the inner ear (e.g. the round window membrane). Exemplary inner ear tissue structures of primary importance for treatment purposes include but are not limited to the cochlea, the endolymphatic sac/duct, the vestibular labyrinth, and all of the compartments (and connecting tubes) which include these components. Access to the above-described inner ear tissue regions is typically achieved through a variety of structures, including but not limited to the round window membrane, the oval window/stapes footplate, the annular ligament, the otic capsule/temporal bone, and the endolymphatic sac/endolymphatic duct, all of which shall be considered "middle-inner ear interface tissue structures" as described in greater detail below. Furthermore, as indicated herein, the middle ear shall be defined as the physiological air-containing tissue zone behind the tympanic membrane (e.g. the ear drum) and ahead of the inner ear.

The inner ear tissues listed above are of minimal size and only readily accessible through microsurgical procedures. In order to treat various diseases and conditions associated with inner ear tissues, the delivery of medicines to such structures is often of primary importance. Representative medicines which are typically used to treat inner ear tissues include but are not limited to urea, mannitol, sorbitol, glycerol, lidocaine, xylocaine, epinephrine, immunoglobulins, sodium chloride, steroids, heparin, hyaluronidase, aminoglycoside antibiotics (streptomycin/gentamycin), antioxidants, neurotrophins, nerve growth factors, various therapeutic peptides, and polysaccharides. Of particular interest in this list are compounds which are used to alter the permeability of the round window membrane within the ear using, for example, hyaluronidase and iontophoretic techniques (defined below). Likewise, treatment of inner ear tissues and/or fluid cavities may involve altering the pressure, volume, electrical activity, and temperature characteristics thereof. Specifically, a precise balance must be maintained with respect to the pressure of various fluids within the inner ear and its associated compartments. Imbalances in the pressure and volume levels of such fluids can cause various problems, including but not limited to conditions known as endolymphatic hydrops, endolymphatic hypertension, perilymphatic hypertension, perilymphatic hydrops, perilymphatic fistula, intracochlear fistula, Meniere's disease, tinnitus, vertigo, hearing loss related to hair cell or ganglion cell damage/malfunction, and ruptures in various membrane structures within the ear.

Of further interest regarding the delivery of therapeutic agents to the middle ear, inner ear, and middle-inner ear interface tissue structures are a series of related and co-owned patents, namely, U.S. Pat. Nos. 5,421,818; 5,474,529, and 5,476,446 all to Arenberg. Each of these patents discloses a medical treatment apparatus designed to deliver fluid materials to internal ear structures. U.S. Pat. No. 5,421,818 describes a treatment system which includes a tubular stem attached to a reservoir portion with an internal cavity designed to retain a supply of therapeutic fluid compositions therein. The side wall of the reservoir portion further comprises fluid transfer means (e.g. pores or a semi-permeable membrane). Contact between the fluid transfer means and the round window membrane in a patient allows fluid materials to be delivered on-demand to the round window membrane, followed by diffusion of the fluid materials through the membrane into the inner ear. U.S. Pat. No. 5,474,529 involves a therapeutic treatment apparatus with a plurality of reservoir portions (e.g. a first and a second reservoir portion in a preferred embodiment) which are connected to multiple tubular stems that are designed for implantation into the endolymphatic sac and duct using standard microsurgical techniques. Finally, U.S. Pat. No. 5,476,446 discloses a therapeutic treatment apparatus which includes a reservoir portion for retaining liquid medicine materials therein, a first tubular stem on one side of the reservoir portion, and a second tubular stem on the opposite side of the reservoir portion. The second stem is designed to reside within the external auditory canal of a patient lateral to the ear drum, while the first stem is sized for placement within an opening formed in the stapes footplate/annular ligament so that medicine materials in fluid form can be delivered into the inner ear from the reservoir portion (which resides in the middle ear cavity medial to the ear drum).

A different approach for transferring materials into and out of the inner ear via the round window membrane/round window niche is disclosed in co-owned pending U.S. patent application Ser. No. 08/874,208 filed on Jun. 13, 1997. This application describes a system in which one or more fluid transfer conduits are provided which are operatively connected to a "cover member" that is designed for placement on top of the niche (e.g. at its point of entry) or within the niche. The cover member is used to create a "fluid-receiving zone" (or "inner ear fluid transfer space") which is partially or entirely sealed in order to facilitate fluid transfer into and out of the inner ear. In one embodiment, the cover member consists of a thin, solid, plate-like structure that is secured in position on top of the niche at its point of entry as previously noted. Alternatively, the cover member may comprise a portion of flexible and compressible material which, during placement within the round window niche, is compressed and thereafter allowed to expand once the portion of compressible material is positioned within the niche. As a result, the cover member can engage the internal side wall of the round window niche, thereby creating the fluid-receiving zone ("inner ear fluid transfer space") between the compressible cover member and the round window niche. Representative materials used to construct the portion of compressible material associated with the cover member in this particular embodiment optimally involve foam-type products including but not limited to polyethylene foam, polyether foam, polyester foam, polyvinyl chloride foam, polyurethane foam, and sponge rubber (e.g. synthetic or natural), all of which are of the closed cell variety, with such materials being non-fluid-absorbent in accordance with the substantial lack of open cells therein. Specifically, the non-fluid-absorbent character of these materials results from the closed cell structure thereof which prevents fluid materials from being absorbed compared with open cell (absorbent) foam products.

Notwithstanding the systems described above, the present invention involves an improved medical treatment apparatus which provides many additional benefits. In accordance with the claimed invention, a unique and specially-designed treatment system is disclosed which is capable of performing a wide variety of basic functions including but not limited to (1) the repeatable and sustained active/passive delivery of therapeutic agents into the inner ear via diffusion or iontophoresis through the round window membrane; (2) the simultaneous measurement of inner ear electrical potentials (evoked or otherwise) using a technique known as "electrocochleography" (hereinafter "ECoG") which is discussed in greater detail below; (3) the controlled withdrawal, exchange, or replacement of inner ear fluid materials via the round window membrane; (4) the delivery of therapeutic fluid compositions to the round window membrane in a manner which is rapid, efficient, controllable, and uses a minimal number of steps and procedures; (5) the transfer of therapeutic fluid compositions to the round window membrane in a highly site-specific manner; (6) the removal of fluid materials from the round window membrane in a localized fashion with minimal losses into adjacent tissue regions; (7) the ability to deliver and withdraw/exchange fluid materials from the inner ear at a precisely controlled rate which is readily undertaken using minimally-invasive surgical procedures; (8) accomplishment of all the above-described goals using a system which is readily applicable to multiple patients having different-sized ear structures; and (9) the ability to readily and instantaneously control placement of the claimed device within the middle ear regions (e.g. the round window niche) of a patient using a highly specialized inflatable "placement control system" which is of primary importance in the present invention. With respect to element number (9) listed above, this unique improvement enables the claimed apparatus to be more readily inserted and removed from a patient, and likewise secures the apparatus in position in a highly stable and rapid manner without requiring the use of adhesive compositions and other comparable attachment systems. Accordingly, the present invention represents an advance in the art of inner ear treatment, diagnosis, and medicine delivery as described in detail below.

SUMMARY OF THE INVENTION

It is an object of the present invention to provide an inner ear fluid transfer and diagnostic system (which can also be therapeutic in character) that enables the efficient delivery of fluid materials (e.g. therapeutic agents) to selected inner ear tissues and tissue regions.

It is another object of the invention to provide a fluid transfer and diagnostic system for treating the inner ear which allows the efficient removal or exchange of fluid materials from selected inner ear tissues and tissue regions.

It is another object of the invention to provide a fluid transfer and diagnostic system for treating the inner ear in which fluid materials are transferred/exchanged into and out of the inner ear directly through middle-inner ear interface tissue structures (e.g. the round window membrane).

It is another object of the invention to provide a fluid transfer and diagnostic system for treating the inner ear which enables the sustained transfer of fluid materials into and out of the inner ear (via the round window membrane) in a controlled, repeatable, and uniform manner.

It is another object of the invention to provide a fluid transfer and diagnostic system for treating the inner ear which facilitates the formation of a partially or completely sealed inner ear fluid-receiving, transfer, and/or exchange zone within the round window niche as further described below.

It is another object of the invention to provide a fluid transfer and diagnostic system for treating the inner ear which enables variable amounts of selected fluid materials to be transferred into and out of the inner ear including microgram/nanogram quantities of such materials (which is especially important when pharmacological agents are being delivered).

It is another object of the invention to provide a fluid transfer and diagnostic system for treating the inner ear which allows the delivery of fluid materials to the round window membrane and the removal of fluid materials therefrom in a highly site-specific manner while avoiding substantial leakage into surrounding tissue regions if desired.

It is a further object of the invention to provide a fluid transfer and diagnostic system for treating the inner ear which is of sufficiently small size to readily facilitate insertion of the claimed apparatus into a patient using minimally-invasive microsurgical procedures.

It is a further object of the invention to provide a fluid transfer and diagnostic system for treating the inner ear which, in one particular embodiment, enables the controlled delivery, exchange, and/or removal of fluid materials from the inner ear via middle ear structures (e.g. the round window membrane) in a manner wherein the fluid materials being delivered are maintained separately from the fluid materials being removed through the use of separate fluid delivery and fluid extraction passageways. As a result, efficient fluid transfer is accomplished while avoiding or minimizing cross-contamination between the fluids being removed and the fluids being delivered. This procedure is especially useful in situations involving drugs or other therapeutic agents which must be supplied in very precise amounts (e.g. microgram and/or nanogram quantities) or when such materials need to be transferred in a given sequence and at controlled time intervals.

It is an even further object of the invention to provide a fluid transfer and diagnostic system for treating the inner ear which has a subsystem (e.g. an electrode assembly) that is capable of delivering and receiving electrical signals (e.g. electrical potentials/electrical current) to and from the inner ear via the round window membrane or other middle ear structures.

It is an even further object of the invention to provide a fluid transfer and diagnostic system for treating the inner ear which, in a preferred embodiment, is capable of rapid placement within and removal from a patient with minimal frictional engagement between the claimed apparatus and the internal ear structures of the patient so that tissue abrasion and patient discomfort are avoided.

It is an even further object of the invention to provide a fluid transfer and diagnostic system for treating the inner ear which is capable of secure engagement within the round window niche of a patient in a minimally invasive manner and without requiring the use of adhesive compositions or other comparable auxiliary attachment systems.

It is an even further object of the invention to provide a fluid transfer and diagnostic system for delivering, receiving, or otherwise transferring fluid materials to and from the ear of a patient in connection with a variety of internal cavities within the ear (whether natural or man-made) in addition to the round window niche as discussed in greater detail below.

The present invention involves a highly effective and minimally-invasive apparatus and method for the controlled and site-specific transfer (e.g. "microdosing") of physician-specified fluid materials into and out of the inner ear via the round window membrane (which is centrally located within the round window niche). The invention described herein offers numerous benefits and represents a significant advance in the art of middle and inner ear diagnosis/treatment. While the invention shall primarily be, discussed herein with reference to the round window membrane/round window niche, it shall also be applicable to other internal cavities within the ear which will become readily apparent from the discussion provided herein. Thus, all of the information presented below regarding use of the claimed apparatus (and all embodiments thereof) within the round window niche shall be incorporated by reference relative to other internal ear cavities (natural or man-made) without limitation. The following summary of the claimed apparatus and method represents a general overview of the invention which outlines the features of primary importance. A more detailed, specific, and enabling disclosure of the invention shall be presented later in the Detailed Description of Preferred Embodiments.

A first embodiment of the claimed invention involves a medical treatment apparatus and method for transferring fluid materials into and out of the inner ear of a human subject. via the round window membrane as previously noted. The apparatus first includes at least one fluid transfer conduit having a first end, a second end, and at least one internal passageway extending through the fluid transfer conduit from the first end to the second end (preferably in a continuous manner). Operatively connected (e.g. fixedly attached in an external, internal, other equivalent fashion as specifically defined below) to at least a portion of the fluid transfer conduit is an inflatable bladder member. The bladder member is preferably located at or adjacent to the first or second end of the conduit on the exterior surface thereof, and is sized for placement within the round window niche of the subject under consideration. The term "placement" as used herein shall involve either partial or entire insertion of the bladder member into the ear cavity of interest (e.g. as much as is needed in accordance with the medical procedure of interest). As will be discussed in greater detail below, the round window niche comprises an internal side wall therein. To secure the apparatus in position within a patient so that fluid materials may be transferred into and out of the inner ear via the round window niche/round window membrane, the bladder member (when inflated and positioned within the round window niche) is designed to engage the internal side wall of the niche. As a result, the bladder member and the portion of the fluid transfer conduit attached thereto are effectively maintained within the niche.

By securing the bladder member and at least part of the fluid transfer conduit within the round window niche, a "fluid-receiving zone" is created inside the niche between the bladder member and the round window membrane which enables rapid, accurate, and site-specific fluid transfer to occur. At the same time, the apparatus is maintained in position in a minimally-invasive manner wherein primary contact/engagement between the tissues of the middle ear and the claimed apparatus only occurs when the bladder member is inflated. Using this approach, dynamic (e.g. sliding) frictional engagement between the claimed apparatus and the tissues of the middle ear during insertion of the apparatus is avoided which controls/reduces irritation, tissue damage, and patient discomfort.

In accordance with the specific system described above, the bladder member again creates a fluid-receiving zone between (1) the bladder member [the upper or external boundary of the fluid-receiving zone]; and (2) the round window membrane [the lower or internal boundary of the fluid-receiving zone]. In physiological terms, this fluid-receiving zone creates a "fluid transfer space" between the bladder member and the round widow membrane within the round window niche. As discussed in considerable detail below, the claimed invention shall not be restricted to any particular size or shape characteristics in connection with the bladder member which may take a number of different forms. For example, the bladder member may be of a sufficiently small size or modified configuration so that, when it engages the internal side wall of the round window niche during inflation, it does not completely seal the fluid receiving zone between the bladder member and the round window membrane. In this particular embodiment, the bladder member may only engage one part of the internal side wall of the niche so that, if necessary in cases of excessive fluid pressure within the fluid-receiving zone, fluid materials can pass in a controlled manner outwardly from the zone (discussed further below).

However, in a preferred embodiment, the bladder member will be configured so that, when inflated, it will completely and circumferentially engage the internal side wall of the round window niche. As a result, a "sealed" fluid-receiving zone is created between (1) the bladder member [the upper or external boundary of the sealed fluid-receiving zone]; and (2) the round window membrane [the lower or internal boundary of the sealed fluid-receiving zone]. By creating a sealed fluid-receiving zone in this manner, the precise delivery (e.g. microdosing) of medicine materials may be accomplished without any fluid leakage outside of the fluid-receiving zone which facilitates a greater degree of delivery precision. Other benefits associated with the creation of a sealed fluid-receiving zone include the maintenance of a controlled pressure environment in order to promote osmotic fluid transfer through the round window membrane as discussed below.

To form a sealed fluid-receiving zone within the round window niche using the inflatable bladder member, all of the components listed above are employed along with a bladder member which is annular (e.g. ring-shaped) so that it completely encircles the fluid transfer conduit at its point of attachment/connection to the conduit. By using a bladder member of this type (which is substantially ring-shaped with a central opening through which the fluid transfer conduit can pass), the bladder member can completely seal the fluid receiving zone by circumferentially engaging the internal side wall of the round window niche as previously discussed. However, the claimed invention shall not be restricted to a bladder member of any size or type which may be varied in accordance with the particular needs of the patient being treated and the desired placement position of the apparatus as determined by routine preliminary testing.

It should also be noted that, unless otherwise stated herein, the present invention and its various embodiments shall not be limited to any particular construction materials. Nonetheless, in a preferred and optimum embodiment, the bladder member will be manufactured from a biologically-inert, medical-grade elastomeric (stretchable) material selected from the group consisting of polyurethane, latex, silicone rubber, and other comparable commercially-available materials which have similar characteristics. Again, a number of different compositions may be employed for this purpose provided that they are capable of stretching sufficiently to achieve the required degree of inflation relative to the round window niche or other middle ear structure/cavity as discussed below. Regarding inflation of the bladder member, at least one "inflation fluid" is pumped into the bladder member for this purpose. The term "fluid" as used herein shall encompass either a gas, a liquid, a gel, or mixtures thereof with this term not being restricted to any particular media materials.

As previously noted, the inflatable bladder member is exteriorly attached to the fluid transfer conduit in a preferred and optimum embodiment. The term "exteriorly attached" and "operatively connected" shall encompass a wide variety of structural configurations including but not limited to adhesive affixation of the bladder member in position on the outer/exterior surface of the fluid transfer conduit. The foregoing phrase shall also encompass a situation in which the bladder member is integrated by molding, heat sealing, and other processes into the side wall of the fluid transfer conduit so that the bladder member forms the outer surface of the conduit which may then be inflated as indicated above. Thus, regardless of the structural configuration which is employed, the bladder member shall be considered "operatively connected" to the fluid transfer conduit as long as it is capable of being inflated in a manner which allows the bladder member to directly engage the internal side wall of the round window niche (or other internal cavity of the ear) so that the conduit can be maintained in a precise and secure position therein. Likewise, the bladder member is operatively connected to the fluid transfer conduit at a position thereon which allows the fluid materials of interest (e.g. compositions transferred to and from round window niche or other desired ear cavity) to freely pass into and out of said apparatus without blockage thereof by the bladder member. This goal is accomplished in a preferred and non limiting embodiment by placement of the bladder member at a chosen location between the first and second ends of the fluid transfer conduit (e.g. on or within the outer surface thereof) or at any other location wherein the bladder member does not entirely block the fluid flow passageway(s) through the fluid transfer conduit as discussed further below. More specifically, the bladder member is preferably oriented whereby it is axially and/or laterally displaced from the fluid flow passageway(s) as shown in the accompanying drawing figures so that the bladder member does not entirely block, plug, or seal such passsageway(s).

All of the embodiments described above (including those with different bladder configurations) may likewise include an "electrical potential transmission system" operatively connected to the fluid transfer conduit. The a term "operatively connected" as used in connection with the electrical potential transmission system can encompass a situation in which this component is attached to the outer/exterior surface of the fluid transfer conduit using adhesive affixation methods, passed through the fluid transfer conduit within one of the passageways therein (including the use of a separate, dedicated passageway for this purpose) or directly incorporated (e.g. molded) into one of the walls of the fluid transfer conduit with all of these connection methods being considered equivalent. The electrical potential transmission system is used to transmit electrical potentials into and out of the inner ear, preferably through the round window membrane. The term "potential" as used herein shall be broadly construed to encompass any type of electrical signal, current, voltage, or impulse regardless of form, magnitude, or origin. In a preferred embodiment discussed in substantial detail below, the electrical potential transmission means will consist of an elongate conductive member (e.g. a metallic wire or strip with a ball, loop, mushroom, flat, or spoon-shaped tip). By placing at least a portion of the elongate conductive member (e.g. a portion which is exposed and not covered by any insulation materials) in direct physical contact with the round window membrane during use of the claimed apparatus (or in contact with tissue materials adjacent thereto which shall be deemed equivalent, namely, the mucosa/bone of the round window niche and others), evoked or non-evoked electrical potentials as defined above may be transmitted to and/or from the membrane for therapeutic analysis and other purposes using various techniques encompassed within the term "electro-cochleography" or "ECoG". Iontophoresis techniques may also be facilitated using the components listed above, with this term being defined to involve a process in which electrical energy is employed to alter the permeability characteristics of the round window membrane to achieve selective fluid transfer and the like. Furthermore, the elongate conductive member may also be used for the purposes listed above in connection with other middle ear tissue structures aside from the round window membrane in order to precisely monitor the tissue materials of interest.

In a still further variation of the claimed apparatus, all of the embodiments discussed above may likewise include at least one semipermeable membrane element operatively attached to the fluid transfer conduit at a position which will enable the membrane to at least partially block the fluid flow passageway(s) therein so that any of the fluid materials to be transferred through the passageway(s) will first need to pass through the membrane. The term "operatively attached" as used herein shall involve a situation in which the membrane is attached in any manner (1) directly to and over the first and/or second end of the fluid transfer conduit; or (2) inside the passageway(s) of the conduit at any position therein. Accordingly, this embodiment of the invention shall not be restricted to any particular placement methods or positions relative to the semipermeable membrane unless otherwise noted herein. Many different materials may be employed in connection with the semipermeable membrane, with the claimed invention not being restricted to any particular construction materials for this purpose. These materials will be listed in the Detailed Description of Preferred Embodiments section. The semipermeable membrane is specifically designed to allow fluid materials (e.g. molecules) being transferred through the conduit to pass into or out of the conduit in a more controlled and uniform manner when desired (e.g. in the case of drug microdosing and other similar situations as discussed further below). In a preferred embodiment, the semipermeable membrane is attached to the end of the fluid transfer conduit that ultimately resides within the fluid-receiving zone located between the inflated bladder member and the round window membrane or other internal ear structure (regardless of whether the fluid-receiving zone is sealed or unsealed). While the use of a semipermeable membrane in connection with the fluid transfer conduit is optional, it is again noted that this particular component is prospectively applicable to all of the specific embodiments recited and covered herein.

At this point, a further discussion of the fluid transfer conduit is in order. As previously indicated, the fluid transfer conduit may consist of a single conduit member having a central passageway therethrough which is designed to accommodate both the delivery of fluid materials to the inner ear via the round window niche/round window membrane and the withdrawal of fluid materials from the inner ear which pass through the round window membrane. In addition to this single-conduit embodiment, the apparatus as claimed shall likewise encompass a system with multiple, individual conduits (e.g. two or more) each having a common (single) inflatable bladder member operatively connected to all of the conduits, with each of the conduits comprising a first end, a second end, and a passageway therethrough. One of these conduits may be used for fluid delivery, with the another conduit being employed for fluid extraction. As a result, cross-contamination of the fluid materials which are entering and leaving the inner ear is avoided which can be important in situations where therapeutic agents (e.g. drugs) need to be delivered in very precise (e.g. microgram, microliter, or nanoliter) amounts over controlled time periods. In a multi-conduit system of the type described above, any of the conduits may likewise include (1) the semipermeable membrane; and/or (2) the electrical potential transmission system associated therewith as previously discussed.

In a still further alternative embodiment, a single fluid transfer conduit may be employed which will nonetheless include multiple (e.g. two or more) passageways (or "lumen") therethrough, all of which are maintained separately from each other. One of these passageways may be used for fluid delivery, with another passageway being employed for fluid extraction. The use of a multiple passageway version of the claimed apparatus is again particularly important in situations where cross-contamination between (1) the fluid materials being delivered into the ear; and (2) the residual fluid materials being removed or exchanged is not desired. This type of system (which is readily manufactured using mass-production techniques) may be used in connection with all of the various bladder designs listed herein in order to provide either a partially or completely sealed fluid-receiving zone. The multi-passageway conduit may likewise include (1) the semipermeable membrane; and/or (2) the electrical potential transmission system associated therewith as previously noted. Either or both of these optional components may again be employed in connection with all of the embodiments discussed herein.

Regarding inflation of the bladder member using the selected inflation fluid (with the term "fluid" being defined above), many different approaches may be employed for this purpose with the present invention not being restricted to any particular inflation method(s). For example, the bladder member can be inflated before or preferably after insertion within the round window niche. Inflation of the bladder member after insertion is preferred since it minimizes frictional engagement between the claimed apparatus and the tissue structures of the middle ear. To accomplish inflation, the bladder member may be "pre-inflated" during the manufacturing process and prior to attachment of this structure to the fluid transfer conduit (or conduits). Alternatively, the bladder member may be inflated during or after insertion of the apparatus into a patient using a separate "inflation fluid delivery conduit" operatively connected to the bladder member. This embodiment will allow the inflation fluid to be delivered directly from an external source into the interior region of the bladder member at a desired rate and amount (discussed further below).

Finally, an efficient, preferred, and space-saving embodiment of the invention will involve the use of a multi-passageway fluid transfer conduit in which one of the passageways is employed to deliver a selected inflation fluid to the bladder member. In this particular embodiment, the bladder member is in fluid communication with at least one of the above-listed passageways through the fluid transfer conduit which is selected for use in delivering the desired inflation fluid to the bladder member. Fluid communication between these components (e.g. the bladder member and the selected passageway within the fluid transfer conduit which shall be designated as an "inflation fluid delivery passageway") will be discussed in greater detail below. However, in a preferred form of the invention, the inflation fluid delivery passageway will terminate at an opening through the side wall of the fluid transfer conduit, with this opening being in substantial registry and communication with a corresponding opening through the main wall of the bladder member. In this manner, a selected fluid may be delivered at a controlled rate to the bladder member so that it can be inflated on-demand (or deflated by reversing this process). This particular embodiment also avoids the use of a separate stand-alone (e.g. exterior) tubular conduit for delivery of the inflation fluid to the bladder member. The inflation system described above may be employed in connection with all of the various bladder members listed herein in order to provide either a partially or completely sealed fluid-receiving zone. Likewise, the foregoing embodiment may optionally incorporate (1) the semipermeable membrane; and/or (2) the electrical potential transmission system associated therewith as previously noted.

All of the various embodiments of the present invention incorporate a common group of features, namely, at least one fluid transfer conduit having an inflatable bladder member operatively connected thereto which permits the claimed apparatus to be inserted and retained within the round window niche of a patient in a secure and minimally-invasive manner. By using the inflatable bladder system discussed above, dynamic (e.g. sliding) frictional engagement between the claimed apparatus and the tissues of the middle ear can be avoided which controls/reduces irritation, tissue damage, and patient discomfort. This type of system also facilitates orientation of the apparatus in a desired position within the ear using minimally-invasive endoscopic placement techniques and permits one device to fit many different-sized niches or cavities. Also, the system of the present invention enables a partially or completely sealed fluid-receiving zone ("inner ear fluid transfer space") to be formed between the bladder member and the round window membrane. As a result, the medicine delivery process (or desired fluid extraction procedure) can occur in a controlled manner which facilitates accurate microdosing, electrocochleography, and/or iontophoresis. This approach therefore represents an advance in the art of ear treatment, diagnosis, and analysis.

A brief summary of the procedures involved in transferring fluid materials into and out of the inner ear using the claimed systems will now be provided. The basic method to be employed in the present invention is equally applicable to all of the embodiments listed above and is likewise applicable to the transfer of fluid materials through all internal ear cavities (with primary reference to the round window niche as discussed below). Regardless of which apparatus is selected for use (e.g. a single fluid transfer conduit with a single passageway therethrough, a single conduit with multiple passageways, or multiple separate conduits), the desired apparatus having the features listed above is initially provided, followed by placement thereof in the middle ear of the patient. Specific methods for accomplishing this step (including the required microsurgical procedures) will be discussed further below in the Detailed Description of Preferred Embodiments section. Next, the bladder member and the portion of the fluid transfer conduit (or conduits) operatively connected thereto are at least partially inserted into the round window niche of the subject. The bladder member is then inflated as previously described using a selected inflation fluid (e.g. a liquid, gas, or gel) so that the bladder member at least partially engages the internal side wall of the round window niche. As a result, the bladder member and the portion of the fluid transfer conduit attached thereto are maintained at least partially inside the niche without requiring adhesives and other attachment systems. By inflating the bladder member after it is placed within the niche, dynamic (e.g. sliding) frictional engagement of the bladder member with middle ear tissues is avoided. This technique again reduces the possibility of frictional abrasion relative to the tissue materials of the middle ear and thereby minimizes (1) patient discomfort; (2) inflammation; and (3) the possibility of infection. However, it may likewise be possible to pre-inflate the bladder member prior to insertion within the round window niche and thereafter place the inflated bladder member inside the niche. The inflated bladder member will then compressively engage the interior side wall of the niche in order to again retain the claimed apparatus in a proper orientation/position within the middle ear. While inflation of the bladder member after insertion inside the niche is preferred for the reasons given above, it is important to emphasize that both inflation methods may be employed with a high degree of effectiveness and shall therefore be encompassed within the present invention as claimed.

Regarding inflation of the bladder member, this step may likewise be accomplished in many different ways as indicated above and further outlined in the Detailed Description of Preferred Embodiments section. The bladder member can again be pre-inflated during manufacture (and prior to attachment to the fluid transfer conduit) or inflated on-demand using a separate stand-alone conduit operatively connected at one end to a supply of inflation fluid and attached at the other end to the bladder member. However, in a preferred embodiment as previously noted, the fluid transfer conduit will include a plurality of passageways therein, one of which will be used to deliver a selected inflation fluid to the bladder member. In this particular embodiment, the bladder member is in fluid communication with the passageway selected for use in delivering the inflation fluid. The inflation fluid can then be transferred through the passageway (e.g. the "inflation fluid delivery passageway") and into the bladder member. As a result, the bladder member will inflate and at least partially engage the internal side wall of the round window niche so that a partially or completely sealed fluid-receiving zone or "inner ear fluid transfer space" is created within the niche between the bladder member and the round window membrane. Whether the fluid-receiving zone is partially or completely sealed will depend on the configuration of the bladder member and the anatomical shape of the adjacent tissue structures under consideration.

After the claimed apparatus is properly inserted in position, the fluid materials of concern are appropriately transferred through the passageway(s) in the fluid transfer conduit as needed and desired. The terms "transfer", "transferring", or "transferred" shall encompass, without limitation, the movement of fluid materials in either direction within the fluid transfer conduit (e.g. either toward the round window niche/round window membrane or away from such structures). For example, these terms may involve the delivery of one or more therapeutic fluid compositions into and through the internal passageway(s) of the fluid delivery conduit (e.g. by conventional hypodermic delivery systems, microsyringes, osmotic mini-pumps, servosyringes, electromechanical pumps, and the like) so that the therapeutic fluid compositions pass through the fluid transfer conduit, enter the fluid-receiving zone within the round window niche, and come in contact with the round window membrane. The therapeutic fluid compositions will then pass through the round window membrane (by diffusion, osmosis, and the like) and move into the inner ear for the treatment thereof. Likewise, any residual fluid materials which remain or otherwise reside within the fluid-receiving zone between the bladder member and the round window membrane (e.g. residual, undiffused therapeutic agents, tissue fluids originating from within the inner ear, and the like) may thereafter or continuously be withdrawn through the internal passageway(s) of the fluid transfer conduit so that they can be removed from the patient. In one embodiment, the withdrawal of residual fluid materials as outlined above is accomplished by applying suction to the second end of the fluid transfer conduit which is remotely spaced from the bladder member and preferably positioned within the external auditory canal of the patient. Likewise, if dual internal passageways are used within the fluid transfer conduit, the delivery of various fluids through one passageway toward the round window membrane may, in fact, force any residual fluid materials already inside the fluid-receiving zone back through another passageway for withdrawal from the patient.

As previously noted, fluid materials can be transferred back and forth through the same internal passageway in a single-passageway conduit, through separate passageways if a multi-passageway conduit is employed, and through separate conduits in a multi-conduit system. Accordingly, the claimed method(s) summarized in this section are equally applicable to all embodiments of the invention.

If a selected electrical potential transmission system (e.g. an elongate conductive member) is used in connection with any or all of the claimed treatment units, electrical potentials (defined above) may be transmitted into and out of the inner ear via the round window membrane by placing at least a portion of the elongate conductive member against and in direct physical contact with the round window membrane. This can be accomplished by appropriate physical manipulation of the selected treatment apparatus within the middle ear as specifically discussed in the Detailed Description of Preferred Embodiments section so that the elongate conductive member comes in contact with the round window membrane. Electrical potentials received from the inner ear via the round window membrane and the elongate conductive member are especially valuable from a diagnostic standpoint, and are recorded/analyzed using an ECoG system operatively connected to the elongate conductive member. It should also be noted that the phrase "direct physical contact with the round window membrane" as it applies to the elongate conductive member shall include placement of this component against internal ear components selected from the group consisting of the round window membrane itself or ear tissue components adjacent to the round window membrane (e.g. the mucosa, bone tissues, and other similar structures which surround the round window membrane).

The use of a semipermeable membrane operatively attached to the fluid transfer conduit as discussed above will also provide a number of important benefits. In a preferred and non-limiting embodiment, the semipermeable membrane will be affixed to the end of the fluid transfer conduit that is ultimately positioned within the fluid-receiving zone between the bladder member and the round window membrane. In this manner, the semipermeable membrane will allow fluid materials being transferred through the conduit to pass into or out of the conduit in a more controlled and uniform manner when desired (e.g. in the case of drug microdosing and other similar situations).

Finally, while use of the present invention shall be discussed herein with primary reference to the round window membrane/round window niche, all embodiments of the invention are equally applicable to placement within other internal cavities in the middle or inner ear of a living subject (either natural or man-made), with examples of these other cavities being provided below. To use the claimed devices within other internal cavities in the ear, the procedures discussed above are followed which are incorporated by reference relative to internal cavities other than the round window niche. Specifically, in a preferred embodiment, the bladder member of the selected apparatus is at least partially placed into the desired internal cavity, followed by inflation of the bladder member in order to maintain the bladder member and the portion of the fluid transfer conduit operatively connected thereto at least partially within the selected internal cavity for the purposes listed above. The same procedure may be employed with a pre-inflated bladder member. Accordingly, unless otherwise stated herein, the present invention shall not be restricted to any particular location or environment within the ear of a living subject.

The present invention represents an advance in the art of inner ear therapy, treatment, and diagnosis. The claimed treatment systems and methods provide numerous benefits and capabilities including: (1) the creation of either a partially or completely sealed fluid-receiving zone ("fluid transfer space") within the round window niche of a patient which enables the controlled and effective delivery of therapeutic fluid compositions to the inner ear via the round window membrane; (2) the delivery of therapeutic fluid compositions to the inner ear using minimally-invasive approaches which are readily accomplished with minimum patient discomfort; (3) the transfer of a wide variety of different therapeutic agents into the middle and inner ear in a sustained, controlled, repeatable, and highly site-specific manner; (4) the removal of fluid materials from the inner ear, the round window niche, and adjacent tissue regions/structures in an efficient and thorough manner using a minimal amount of equipment and operating components; (5) the ability to electrocochleographically monitor evoked and non-evoked signals/potentials coming from the inner ear while simultaneously delivering therapeutic agents so that the effect of such agents can immediately determined before, during, or after delivery of the agents; (6) the more efficient use of iontophoretic techniques in inner ear therapy; (7) transmission into the middle and inner ear of various electrical signals for treatment purposes and/or the diagnostic, electrophysiological analysis of internal ear structures; (8) the ability to readily control placement of the claimed device within the round window niche of a patient using a highly specialized, fluid-inflatable "placement control system" in the form of a bladder member that is designed to engage the internal side wall of the round window niche (or other selected internal ear cavity); and (9) the development of a unique, multi-functional, "one-size-fits-all" inner ear treatment and diagnostic system which enables all of the foregoing benefits to be achieved using a minimal amount of components, procedures, equipment, and technical personnel. With respect to element number (8) listed above, this unique improvement enables the claimed apparatus to be more readily inserted and removed from a patient, and likewise secures the apparatus in position in a highly stable manner without requiring the use of adhesive compositions or other attachment systems. The invention as discussed herein is readily applicable to living subjects of different age, size, and internal ear tissue configurations. For these reasons and the other reasons listed below, the claimed invention represents a substantial advance in the art of otological treatment and diagnosis.

These and other objects, features, and advantages of the invention will become readily apparent from the following Brief Description of the Drawings and Detailed Description of Preferred Embodiments.

Figure 1:
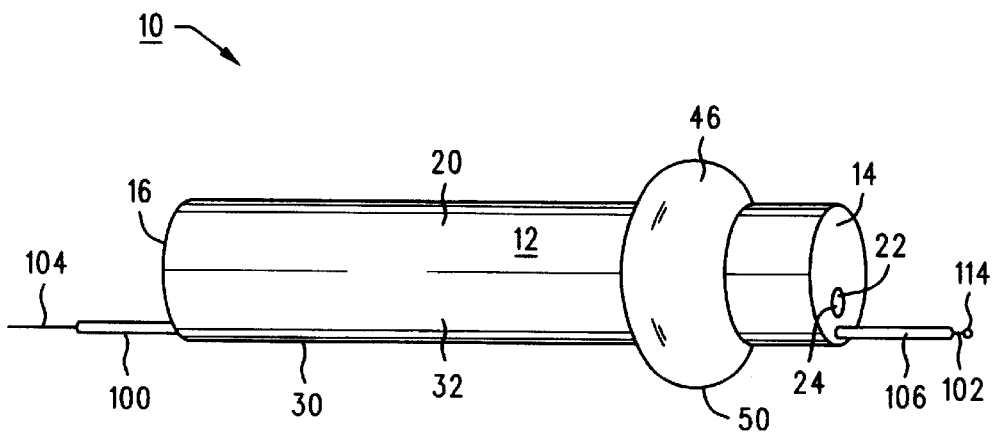
FIG. 1 is a front perspective view in enlarged format of a primary embodiment of the claimed fluid transfer and diagnostic apparatus wherein the bladder member is illustrated in an inflated state.

It should also be noted that common reference numbers employed in all of the drawing figures discussed below shall signify the use of common structural components in connection with the numbered elements under consideration.

DETAILED DESCRIPTION OF PREFERRED EMBODIMENTS

As noted above, the present invention involves a unique and highly effective method for transferring fluid materials into and out of the inner ear via the round window membrane (and other internal ear cavities). The "round window membrane" consists of a thin, cellular membrane structure positioned within a cavity in the middle ear known as the "round window niche". Both of these structures are illustrated and discussed in U.S. Pat. No. 5,421,818 which is incorporated herein by reference. The round window membrane has a number of important physical features including a semi-permeable character that enables fluid materials (e.g. molecules) to be readily transferred across the membrane by diffusion, osmosis, active transport, and the like as outlined further below. The round window membrane provides a number of unique opportunities regarding the transfer of fluid materials into and out of the inner ear through the membrane. For the purposes of this invention, both the round window membrane and the round window niche shall collectively be designated herein as "middle-inner ear interface tissue structures". Likewise, the middle ear shall again be defined as the physiological air-containing tissue zone behind the tympanic membrane (e.g. the ear drum) and ahead of the inner ear. The "inner ear" basically consists of those portions of the ear contained within the otic capsule and the temporal bone which is the most dense bone tissue in the entire human body. Exemplary inner ear tissue structures of primary importance include but are not limited to the cochlea, the endolymphatic sac/duct, the vestibular labyrinth, and all of the compartments/connecting tubes which include or contain any of these components.

In order to treat various diseases and conditions associated with the inner ear, the delivery of medicines thereto is of primary importance. Representative medicines (also designated herein as "therapeutic fluid compositions") which are-typically used to treat inner ear tissues include but are not limited to urea, mannitol, sorbitol, glycerol, lidocaine, xylocaine, epinephrine, immunoglobulins, sodium chloride, steroids, heparin, hyaluronidase, aminoglycoside antibiotics (streptomycin/gentamycin), antioxidants, neurotrophins, nerve growth factors, various therapeutic peptides, and polysaccharides. Likewise, the treatment of inner ear tissues and/or fluids may involve altering the pressure, volumetric, and temperature characteristics thereof. As previously noted, a precise balance must be maintained in connection with the pressure of various fluids inside the inner ear and its associated compartments. Imbalances in inner ear fluid pressure levels can cause numerous problems, including but not limited to conditions known as endolymphatic hydrops, endolymphatic hypertension, perilymphatic hypertension, Meniere's disease, and perilymphatic hydrops.

It is a goal of this invention to provide an effective apparatus and method for transferring fluid materials into and out of the inner ear with a minimal degree of complexity and surgical intervention. The term "fluid materials" shall not be limited to any particular compositions and will include drugs and biologics, as well as liquid materials (e.g. molecules) produced within the ear itself. Likewise, "fluid materials" shall encompass solid-power compositions which, when administered to the target tissues of interest, are converted in situ to liquid compositions using either added liquids provided from an outside source or natural fluids within the ear. Thus, the term "fluid materials" shall not be restricted in any manner and will also be defined to encompass both liquids, gases, and gel-type compositions.

It is likewise a goal of the invention to provide an apparatus and method which create a partially or completely sealed "fluid-receiving zone" (also known as an "inner ear fluid transfer space" or simply a "fluid transfer space") within the middle ear ahead of the round window membrane. Within the fluid-receiving zone, various fluids can be delivered to and/or withdrawn from the inner ear via the round window membrane. As discussed in substantial detail below, this will be accomplished by selectively blocking the round window niche using an inflatable bladder member in order to create the fluid-receiving zone between (1) the bladder member [which shall define the upper boundary of the fluid-receiving zone]; and (2) the round window membrane [which shall define the lower boundary of the fluid-receiving zone]. Fluid materials are delivered into and/or withdrawn from the fluid-receiving zone by at least one tubular conduit having one or more passageways therethrough, with the bladder member being operatively connected to the conduit. This unique process and the creation of a fluid-receiving zone within the round window niche provides a number of important benefits including the ability to precisely control and monitor the transfer of fluids into and out of the inner ear. Finally, the inflatable bladder member (which is designed to at least partially engage the internal side wall of the round window niche) constitutes a "placement control system" which enables the claimed apparatus to be securely maintained in position within the round window niche of a patient by simply inflating the bladder member with a selected "inflation fluid" on-demand. This particular system enables the apparatus to be more readily inserted and removed from a patient, and likewise secures the apparatus in position without the required use of adhesive compositions or other auxiliary attachment systems. For these reasons and the other reasons given below, the present invention therefore represents a significant advance in the art of inner ear treatment and diagnosis.

A. Fluid Treatment and Diagnostic Devices of the Present Invention

A number of different devices produced in accordance with the invention may be employed to achieve the goals listed above. Various embodiments of the claimed inner ear fluid transfer and diagnostic system will first be discussed in detail. Thereafter, the manner in which these systems are used in a living subject will be described. It should be noted at this time that all of the dimensions listed below are provided for example purposes only and shall not be regarded as limiting.

Figure 2:
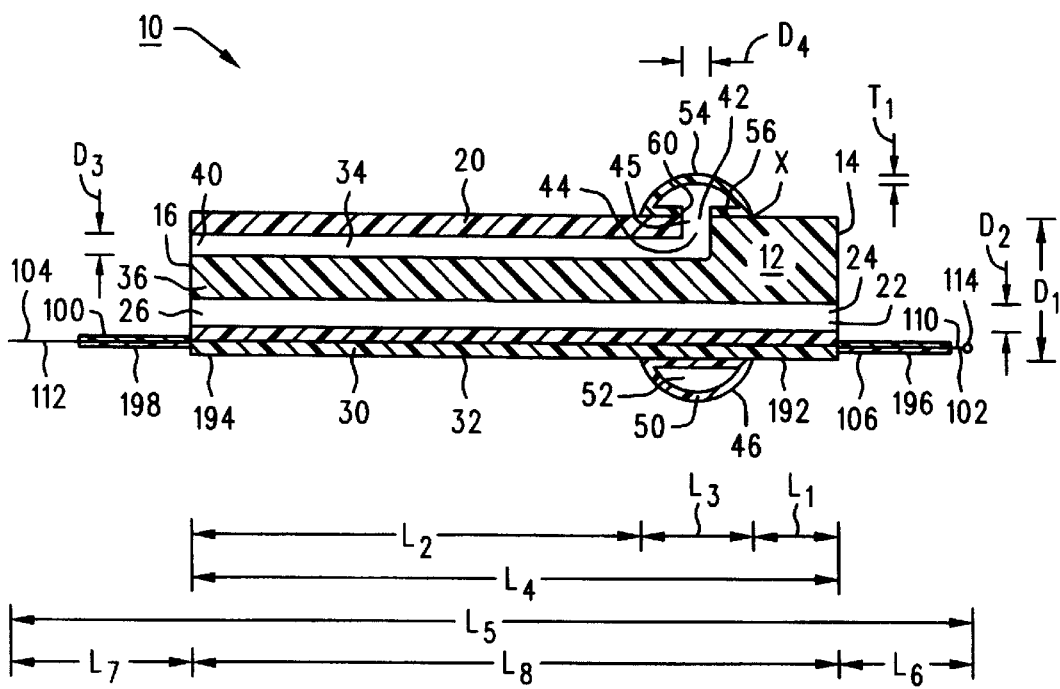
FIG. 2 is a cross-sectional view in enlarged format of the apparatus of FIG. 1.

With reference to FIGS. 1 and 2, a treatment apparatus 10 is schematically illustrated in enlarged format for the sake of clarity. As shown in FIGS. 1 and 2, the apparatus 10 includes at least one fluid transfer conduit 12 which is designed to allow fluid materials to be transferred toward and/or away from the round window membrane/round window niche (e.g. the fluid-receiving zone) or other selected internal ear cavity as discussed in greater detail below. The fluid transfer conduit 12 specifically includes an open first end 14, an open second end 16, and a medial portion 20 between the first and second ends 14, 16 (FIGS. 1–2). In addition, the fluid transfer conduit 12 is tubular in construction, with the term "tubular" being defined to encompass a structure which includes at least one or more central passageways therethrough that are surrounded by an outer wall. As will become readily apparent from the discussion provided below, the fluid transfer conduit(s) of the present invention may have any number of passageways therethrough, with the invention not being limited in this regard. As illustrated in the embodiment of FIG. 2, a single fluid flow passageway 22 is provided which extends continuously through the fluid transfer conduit 12 from the open first end 14 to the open second end 16. The passageway 22 further includes an open proximal end 24 located adjacent the first end 14 of the conduit 12 and an open distal end 26 (FIG. 2) located adjacent the second end 16 of the conduit 12. Surrounding the fluid flow passageway 22 is a side wall 30 having an outer (e.g. exterior) surface 32. It should be noted at this time that the term "proximal" is used throughout this description in connection with components/structures associated with the apparatus 10 which are closest to the inner ear when the apparatus 10 is inserted in a patient. Conversely, "distal" shall refer to components/structures associated with the apparatus 10 which are farthest from the inner ear when the apparatus 10 is positioned within the patient.

The fluid transfer conduit 12 is optimally circular in cross-section with a uniform external diameter "$D_1$" (FIG. 2) of about 0.5–2.0 mm. Likewise, in a preferred embodiment, the passageway 22 through the conduit 12 will have a uniform internal diameter "$D_2$" (FIG. 2) of about 0.2–0.8 mm which is sufficient to allow the adequate passage of fluid compositions therethrough in either direction.

With continued reference to the embodiment of FIG. 2, the fluid transfer conduit 12 likewise includes an optional (but preferred) inflation fluid transfer passageway 34 which is designed to deliver a selected inflation fluid (e.g. a gas, liquid, or gel as defined above) to the inflatable bladder member associated with the apparatus 10 as discussed in considerable detail below. The inflation fluid transfer passageway 34 is entirely separate from the fluid flow passageway 22 and begins at the second end 16 of the fluid transfer conduit 12 where it is open and able to receive the selected inflation fluid. It should also be noted that, in a preferred embodiment, the inflation fluid transfer passageway 34 will have slightly smaller size/dimension characteristics than the main fluid flow passageway 22. For example, the passageway 34 through the conduit 12 will optimally have a uniform internal diameter "$D_3$" of about 0.01–0.1 mm (FIG. 2) which is sufficient to allow the adequate passage of one or more inflation fluid compositions therethrough.

A cross-sectional view of the fluid transfer conduit 12 having passageways 22, 34 therein is provided in FIG. 2. Both passageways 22, 34 are separated from each other by an integrally-formed barrier portion 36 which is positioned between the passageways 22, 34 and formed during the extrusion or other processes which are employed to produce the fluid transfer conduit 12.

With continued reference to FIG. 2, the inflation fluid transfer passageway 34 includes an open distal end 40 located adjacent the second end 16 of the fluid transfer conduit 12. The inflation fluid transfer passageway 34 also comprises an open proximal end 42 that does not terminate at the first end 14 of the conduit 12 but instead stops ahead of the first end 14 within the medial portion 20 of the conduit 12 at position 44. At position 44, the inflation fluid transfer passageway 34 turns upwardly at a preferred angle of about 90° and terminates at an opening 45 (FIG. 2) through the side wall 30 of the fluid transfer conduit 12. The function of the opening 45 will be discussed in greater detail below.

Representative biologically-inert construction materials which may be employed in connection with the fluid transfer conduit 12 (which is preferably of single-piece "unitary" construction) include but are not limited to silicone rubber, latex rubber, and plastic. The term "plastic" as used herein shall encompass a wide variety of compositions including polycarbonate, polyester, polyethylene, polypropylene, polyvinyl chloride, nylon, and other comparable materials. It should again be noted that the claimed invention and its various components shall not be restricted to any specific dimensions, construction materials, and other parameters unless otherwise expressly stated herein. All of these items may be selected in accordance with a variety of factors including the intended use of the apparatus and the specific conditions being treated.

As shown in FIGS. 1–2, the fluid transfer conduit 12 is operatively connected to a structure designated herein as an "inflatable bladder member" 46. The term "operatively connected" used in connection with the bladder member 46 and the fluid delivery conduit 12 (or any other conduits discussed herein) shall encompass any attachment configuration which enables the bladder member 46 to be mounted in position relative to the conduit 12 so that both of these components are securely attached together. In this regard, "operative connection" of the fluid transfer conduit 12 and bladder member 46 to each other shall include but not be limited to (1) attachment of the bladder member 46 to the outer surface 32 of the side wall 30 associated with the fluid transfer conduit 12; and (2) direct integration of the bladder member 46 into the side wall 30 of the conduit 12. Both of these alternatives shall be deemed equivalent and collectively encompassed within the terms "exteriorly attached" and "operatively connected" relative to the conduit 12. However, in a preferred embodiment and for the sake of clarity, the apparatus 10 illustrated in FIGS. 1–2 shall involve attachment of the bladder member 46 to the outer surface 32 of the side wall 30 associated with the fluid transfer conduit 12.

Likewise, the bladder member 46 is operatively connected to the fluid transfer conduit 12 at a position thereon which allows the fluid materials of interest (e.g. compositions transferred to and from round window niche or other desired ear cavity) to freely pass into and out of the apparatus 10 without blockage thereof by the bladder member. This goal is accomplished in a preferred and non-limiting embodiment by placement of the bladder member 46 at any chosen location between the first and second ends 14, 16 of the fluid transfer conduit 12 (e.g. on or within the side wall 30 along the medial portion 20 thereof) or at any other location wherein the bladder member 46 does not entirely block the fluid flow passageway(s) through the fluid transfer conduit (e.g. passageway 22 in the embodiment of FIGS. 1–2.) The bladder member 46 is preferably oriented whereby it is axially and/or laterally displaced from the fluid flow passageway(s) through the conduit 12 as shown in all of the drawing figures so that the bladder member 46 does not entirely block, plug, or seal such passsageway. Accordingly, the present invention shall not be restricted to any particular orientation relative to the bladder member 46 provided that the bladder member 46 does not completely block the passage of fluid materials into and out of the apparatus 10 for delivery to the round window niche or other selected ear cavity.

The bladder member 46 includes an outer (e.g. exterior) wall 50 which surrounds an internal cavity 52 that is designed to receive at least one inflation fluid therein as discussed in further detail below. The outer wall 50 of the bladder member 46 optimally has a uniform thickness "$T_1$" (FIG. 2) of about 0.01–0.40 mm although the present invention shall not be restricted to this range which is provided for example purposes and will depend to a significant extent on the particular material that is used to construct the bladder member 46. The selected construction material associated with the bladder member 46 should be highly stretchable and resilient in order to allow the bladder member 46 to readily expand (e.g. inflate) during use of the apparatus 10 for its intended purposes. In this regard, representative compositions which are suitable for producing the bladder member 46 shall include but not be limited to a biologically-inert, medical-grade elastomeric (stretchable) material selected from the group consisting of polyurethane, latex, silicone rubber, and other comparable commercially-available materials which have similar characteristics. To achieve a maximum degree of operational efficiency, the inflatable bladder member 46 (e.g. the internal cavity 52) will optimally have an internal volumetric capacity (uninflated) of about 0.1–0.4 cc which, after inflation, is capable of increasing by about 25–100% to about 0.3–1.0 cc. In accordance with this design, the bladder member 46 will be able to inflate and fill/engage the desired cavity within the ear (e.g. the round window niche or other region) as discussed in further detail below.

It is noted in FIGS. 1–2 that the bladder member 46 has an ovoid "doughnut-like" shape. However, the present invention shall not be restricted to this design which is provided for example purposes only. The bladder member 46, in the alternative, may be substantially more spherical if desired in accordance with preliminary testing involving the particular patient of concern and the intended uses of the apparatus 10. In the embodiment of FIGS. 1–2, the bladder member 46 (irrespective of its particular shape as discussed in detail below) is pre-manufactured and thereafter slipped over and onto the conduit 12, followed by attachment to the conduit 12 at position "X" on the outer surface 32 of the side wall 30 using a variety of possible methods. These methods include but are not limited to the use of conventional adhesive materials applied to the outer surface 32 of the side wall 30 of conduit 12, the exterior surface 54 of the outer wall 50 associated with the bladder member 46, or both of these components. Representative adhesive compositions suitable for this purpose include but are not limited to standard epoxy and/or cyanoacrylate adhesives known in the art. Attachment of the foregoing components together may also occur using conventional thermal welding techniques and the like during production of the apparatus 10. Thus, the present invention shall not be restricted to any particular attachment methods which may be employed to affix the bladder member 46 to the fluid transfer conduit 12.

In the embodiment of FIG. 2, a particular and unique interaction of components is illustrated which enables inflation of the bladder member 46 to occur in a highly effective manner. This particular design will now be discussed in greater detail. With reference to FIG. 2, the outer wall 50 of the bladder member 46 further includes a bottom section 56 which is engaged directly against and in contact with the outer surface 32 of the side wall 30 associated with the fluid transfer conduit 12 at position "X" as illustrated. Likewise, the bottom section 56 includes an opening 60 passing therethrough which (in a preferred embodiment) is substantially the same size/diameter as the opening 45 through the side wall 30 of the fluid transfer conduit 12. As previously noted, the opening 45 in the side wall 30 constitutes the point of entry into the proximal end 42 of the inflation fluid transfer passageway 34. Both of the openings 45, 60 may be of any size/diameter which is sufficient to allow the passage of an inflation fluid therethrough so that the bladder member 46 can be properly inflated on demand. In a representative and non-limiting embodiment, openings 45, 60 shall be circular in configuration and have a equal, uniform diameter "$D_4$" (FIG. 2) of about 0.5–3.5 mm. Likewise, to facilitate proper flow of the selected inflation fluid into and out of the internal cavity 52 of the bladder member 46 via the inflation fluid transfer passageway 34, both of the openings 45, 60 as shown in FIG. 2 shall optimally be in substantial registry with each other.

Inflation of the bladder member 46 will be discussed in greater detail below. However, with reference to FIGS. 2 and 8, the distal end 40 of the inflation fluid transfer passageway 34 is operatively connected using conventional adhesive materials (e.g. standard cyanoacrylate or epoxy adhesives, and the like), frictional engagement, thermal welding, or a combination of these techniques to the first end 62 of a tubular inflation fluid transfer conduit 64. The conduit 64 terminates at a second end 66 that is remotely spaced from the first end 62 (and is preferably located outside the ear of the patent/living subject being treated). These structures have been omitted from FIG. 2 for the sake of clarity but, as noted above, are illustrated in FIG. 8. The inflation fluid transfer conduit 64 (which is optimally produced from the same materials listed above in connection with the fluid transfer conduit 12 and may be of any suitable size taking into consideration the particular living subject involved) likewise comprises an internal passageway 70 which extends continuously through the conduit 64 from the first end 62 to the second end 66. The second end 66 of the conduit 64 is attached to a supply of inflation fluid 72 which resides within a selected delivery apparatus 74. The present invention shall not be restricted to any particular type of delivery apparatus 74 provided that the apparatus 74 is capable of delivering/transferring the inflation fluid 72 to the bladder member 46 in a manner which causes the bladder member 46 to inflate as previously discussed. Representative systems which may be used in connection with the delivery apparatus 74 include, without limitation, conventional hypodermic syringe systems, micro-pumps, and other equivalent fluid transfer units.

In a preferred embodiment the delivery apparatus 74 should be capable of delivering/transferring the selected inflation fluid 72 at a rate of at least about 0.025–1.0 cc per minute, with this value being presented in a non-limiting manner for example purposes only. Likewise, while the apparatus 74 is designated herein as a "delivery" apparatus 74 it should also be capable of withdrawing (or allowing the withdrawal of) the inflation fluid 72 from the bladder member 46 in order to achieve deflation of the bladder member 46 when needed and appropriate (e.g. after treatment of the patient is completed and removal of the apparatus 10 is desired). To achieve this goal, the delivery apparatus 74 should be capable of actively or passively withdrawing (or enabling the withdrawal of) the inflation fluid 72 from the bladder member 46 via the inflation fluid transfer passageway 34 of the conduit 12 and the internal passageway 70 of the conduit 64. All of the particular devices listed above in connection with the delivery apparatus 74 (e.g. pumps, hypodermic systems, etc.) can accomplish this goal in an effective manner.

Figure 8:
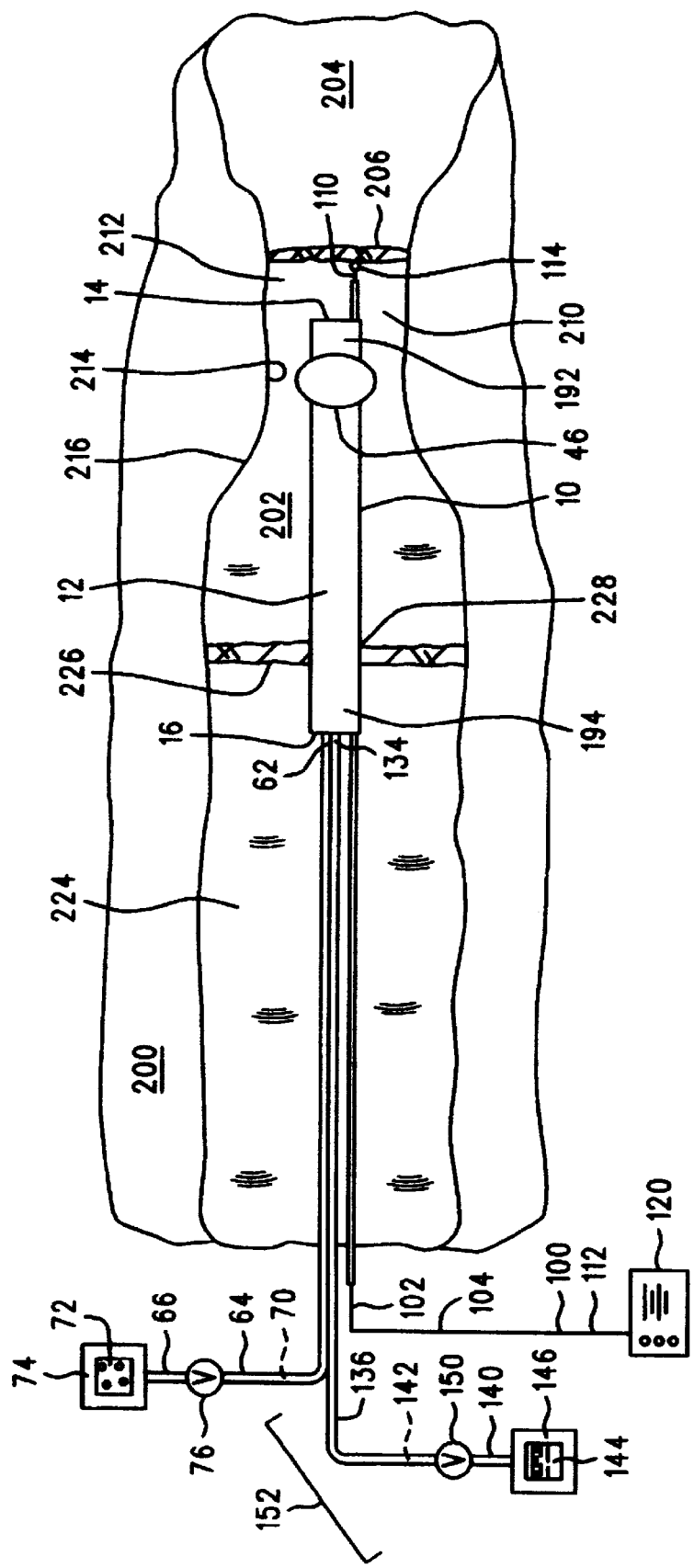
FIG. 8 is a schematic representation of the fluid transfer and diagnostic apparatus of FIGS. 1–2 positioned within the ear of a human subject prior to inflation of the bladder member.

In addition, to properly maintain inflation of the bladder member 46 over prolonged time periods (and to generally control transfer of the inflation fluid 72 into and out of the bladder member 46), the inflation fluid transfer conduit 64 may include an optional control valve schematically illustrated in FIG. 8 at reference number 76. The valve 76 (which is typically of a conventional rotary, ball, or other type) may be integrally positioned in-line within the inflation fluid transfer conduit 64 or alternatively can be integrated directly into the delivery apparatus 74 or inflation fluid transfer passageway 34, depending on the type of apparatus 74 under consideration. Also, it should again be emphasized that the valve 76 is optional and shall be selected for use in accordance with preliminary pilot studies on the particular overall system and living subject(s) under consideration.

Many different materials may be employed in connection with the inflation fluid 72, with the claimed invention not being restricted to any particular composition(s) for this purpose. As previously noted, the term "fluid" as used herein shall encompass either a gas (e.g. air, $N_2$, "carbogen" [e.g. a mixture of $O_2$ and $N_2$], $O_2$), a liquid (e.g. water, saline, artificial perilymph, "lactated Ringers" solution), a gel (e.g. in paste, dry-mix, or anhydrous form), or mixtures thereof. In a representative and non-limiting embodiment, a preferred inflation fluid 72 will consist of air delivered at ambient temperature levels of about 20–23° C. Again, many different materials may be employed for this purpose which shall be selected in accordance with preliminary testing involving the particular system under consideration.

At this time, further information will be presented regarding the overall configuration of the bladder member 46 and variants thereof which are encompassed within the claimed apparatus 10. With reference to the end view of FIG. 3, the front face 80 of the bladder member 46 is illustrated with the open first end 14 of the fluid transfer conduit 12 passing therethrough. The first end 14 is considered to be "open" since the fluid flow passageway 22 passes therethrough and terminates at the first end 14. The longitudinal cross-sectional design of the bladder member 46 in both an inflated and uninflated (e.g. deflated) state is circular/spherical (FIG. 3), with the bladder member 46 completely encircling the fluid transfer conduit 12. As a result, when inflated, the bladder member 46 will circumferentially engage the internal side wall of the round window niche in the living subject being treated (discussed further below). A "sealed" fluid-receiving zone will thus be created between (1) the bladder member 46 [the upper or external boundary of the sealed fluid-receiving zone]; and (2) the round window membrane [the lower or internal boundary of the sealed fluid-receiving zone]. By creating a sealed fluid-receiving zone in this manner, the precise delivery (e.g. microdosing) of medicine materials may be accomplished without any substantial fluid leakage outside of the fluid-receiving zone which facilitates a greater degree of delivery precision. Other benefits associated with the creation of a sealed fluid-receiving zone include the maintenance of a controlled pressure environment in order to promote osmotic fluid transfer through the round window membrane as outlined below.

Figure 3:
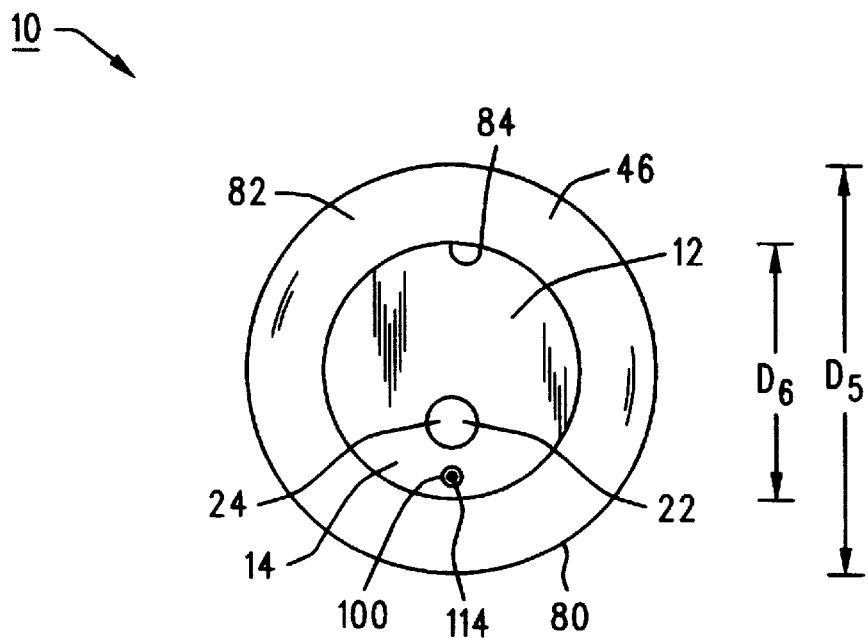
FIG. 3 is an end view in enlarged format of the apparatus of FIGS. 1–2 specifically illustrating the inflatable bladder member of the apparatus which is annular in configuration.

In accordance with the embodiment of FIG. 3, the bladder member 46 will be designated herein as "annular" or ring-shaped with a main body portion 82 and a central opening 84 passing therethrough to form a "doughnut-like" configuration. As shown in FIG. 3, the body portion 82 of the bladder member 46 will have a representative and non-limiting diameter "$D_5$" of about 0.3–2.0 mm when uninflated (and about 1.0–5.0 mm after inflation) although these values may be varied as needed in accordance with the particular physical parameters of the ear structures in the living subject of concern as determined by preliminary examination. In this regard, the claimed invention shall not be restricted to a bladder member 46 of any size, type, or shape which may be varied in accordance with the particular needs of the patient being treated. It should also be noted that the diameter "$D_6$" of the central opening 84 through the main body portion 82 of the bladder member 46 will optimally be about 5–10% less than the diameter $D_1$ of the fluid transfer conduit 12 as discussed above (FIG. 2). This design configuration assists in secure attachment (e.g. frictional engagement) between the foregoing components and is accomplished in accordance with the flexible/stretchable nature of the materials used to produce the bladder member 46 as listed above. Accordingly, in a preferred embodiment, the diameter "$D_6$" of the central opening 84 will optimally be about 0.3–1.5 mm (uninflated) which will readily enable the bladder member 46 to be "slipped" onto the first end 14 of the conduit 12 during assembly/production of the apparatus 10. Furthermore, for reference purposes, the average diameter of the round window niche in a typical human adult subject is about 1.2–2.5 mm (which indicates that the bladder member 46 is readily inserted into the niche in an uninflated state and will thereafter properly engage the internal side wall of the niche when inflated as discussed below.) The niche in children may, in fact, be smaller.

Figure 4:
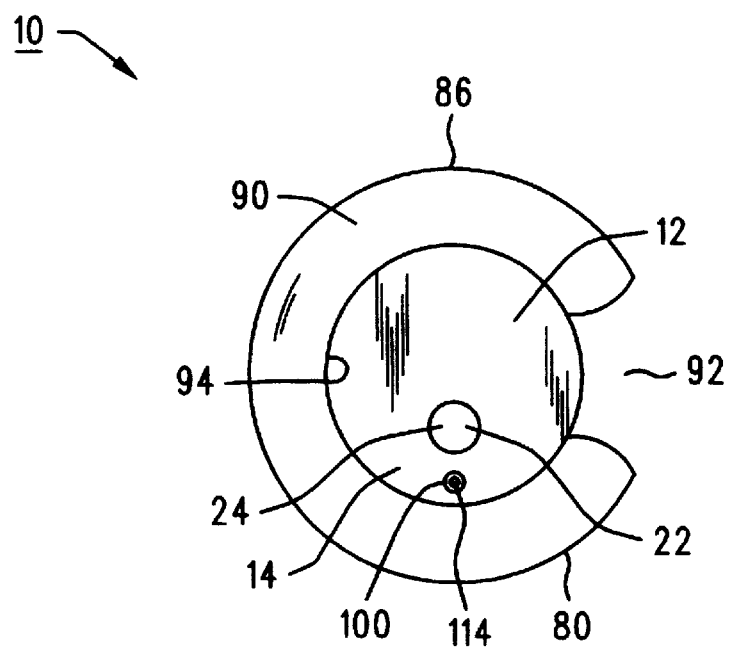
FIG. 4 is an end view in enlarged format of an alternative embodiment of the apparatus of FIGS. 1–2 specifically illustrating the inflatable bladder member of the apparatus (in an inflated state) which is non-annular in configuration.

While the use of an annular bladder member 46 in the embodiment of FIG. 3 is preferred as discussed above, other bladder configurations are also possible and encompassed with the system described herein. With reference to FIG. 4, an end view of another bladder design is shown. All of the information, data, size/volume/diameter parameters, construction materials, and other items presented above in connection with the bladder member 46 shown in FIGS. 1–3 are equally applicable to the alternative bladder member 86 illustrated in FIG. 4 and shall be incorporated by reference in this section with one exception. Specifically, the alternative bladder member 86 of FIG. 4 shall not be considered "annular" in configuration since it does not completely encircle the fluid transfer conduit 12. Instead, it consists of a body portion 90 which is substantially "U-shaped" with an open region 92. Positioned within the open region 92 is a circular wall 94 that is designed for operative connection to (and snug, conforming engagement with) the outer surface 32 of the side wall 30 associated with the fluid transfer conduit 12 using the attachment techniques discussed above in connection with the bladder member 46. The wall 94 will preferably include an opening therein (not shown) which is equivalent in size and overall configuration to the opening 60 through the bladder member 46 in the embodiment of FIGS. 1–3 so that the bladder member 86 of FIG. 4 can be inflated in the same manner described above.

The "partially open" design associated with the non-annular bladder member 86 of FIG. 4 is designed to provide a barrier within the round window niche (or other cavity) of the living subject which is not entirely fluid-tight (e.g. not a complete seal). When inflated using the system discussed above in connection with the bladder member 46, the alternative bladder member 86 will not completely (e.g. circumferentially) engage the internal side wall of the round window niche. As a result, while the non-annular bladder member 86 will assist in keeping various fluids between the bladder member 86 and the round window membrane (discussed below), fluid materials may also pass through the open region 92 if desired and needed. This particular embodiment is used in situations where excessive fluid pressures in the ear (particularly adjacent the round window membrane) are not desired. Specifically, the embodiment of FIG. 4 avoids the build-up of excessive pressure levels in the middle ear by providing an "escape route" for fluid materials should they begin to accumulate and exert pressure on the round window membrane and tissue materials adjacent thereto. Regarding the use of a non-annular bladder member as discussed above, it is important to emphasize that the previously-described goals associated with this embodiment may be accomplished using a number of different non-annular (or non-"U-shaped") bladder designs provided that, in some manner, an "open region" is created which provides an escape route for accumulated fluid materials. Other non-annular bladder members designed for operative connection to the fluid transfer conduit 12 shall encompass a wide variety of different designs including spherical or ovoid bladders attached on only one side of the conduit 12 and the like. Also, a large ring-shaped bladder may be used which is configured so that the diameter of the central opening therethrough (e.g. opening 84 as shown in FIG. 3) is much larger than the diameter of the fluid transfer conduit 12 which allows fluid materials to flow therebetween. Bladder members of the type shown in FIG. 4 which include an open region 92 shall also not be restricted to any particular size or shape. Likewise, a circular, ring-like bladder may be employed which does not necessarily include the open region 92 therein but instead comprises a small "dent" or indentation in the surface to allow fluids to pass. In this regard, unless otherwise stated herein, the claimed system shall not be limited to any particular bladder shapes or configurations.

As previously indicated, all of the information provided herein concerning inflation of the bladder member 46 shown in FIGS. 1–3 shall again be applicable to the other bladder designs discussed above, including but not limited to the alternative bladder member 86 of FIG. 4. In addition to the system shown in FIG. 2 which involves the use of a separate inflation fluid transfer passageway 34 through the fluid transfer conduit 12 to inflate the bladder member 46 on-demand, it should be noted that the bladder member 46 may be produced and supplied in a "pre-inflated" state so that inflation thereof during use is not needed. While the overall ability to selectively inflate the bladder member 46 during use of the apparatus 10 is generally preferred in order to provide a more efficient fluid transfer system, a pre-inflated bladder member 46 may be employed in cases where (1) rapid insertion and removal of the apparatus 10 is desired; and/or (2) the need for precise conformity of the bladder member 46 with the internal ear structures under consideration is not of primary importance. This information also applies to bladder member 86.

Figure 5:
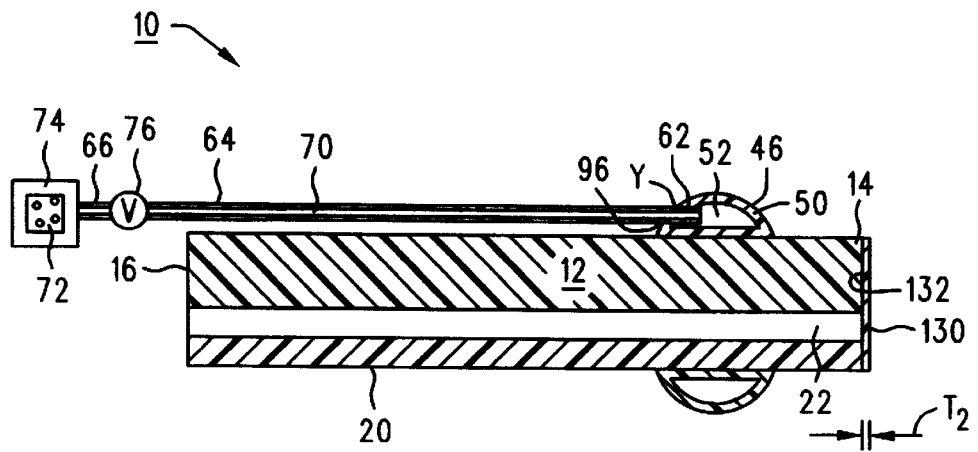
FIG. 5 is a cross-sectional view in enlarged format of a further alternative embodiment of the apparatus of FIGS. 1–2 which incorporates an external conduit delivery system for supplying inflation fluid to the bladder member of the apparatus (shown in an inflated state) compared with the internal conduit delivery system for supplying inflation fluid to the bladder member in the embodiment of FIG. 2.

Another inflation method which may be employed in connection with the apparatus 10 is schematically illustrated in FIG. 5. Basically, all of the information, features, components, and numerical design parameters discussed above in connection with the embodiments of FIGS. 1–4 are equally applicable to the embodiment of FIG. 5 except as otherwise noted herein. With reference to FIG. 5, all of the structural components shown therein are the same as those illustrated in FIG. 2 except for the particular system which is employed to inflate the bladder member 46. Specifically, the inflation fluid transfer passageway 34 is entirely omitted from the apparatus 10 of FIG. 5 along with its various structural components. In place of this "internal" system, an "external" inflation fluid delivery conduit is provided as illustrated. Specifically, the inflation fluid transfer conduit 64, the supply of inflation fluid 72, the delivery apparatus 74, the valve 76, and all of the other components and information presented above relative to the embodiment of FIG. 2 (e.g. as shown in FIG. 8) are carried over into the embodiment of FIG. 5. However, instead of connecting the first end 62 of the conduit 64 to the inflation fluid transfer passageway 34, the first end 62 of the conduit 64 is operatively connected in a direct manner to the outer wall 50 of the bladder member 46 at position "Y" thereon (FIG. 5). Specifically, the bladder member 46 at position "Y" has an opening 96 passing therethrough which is sized to receive the first end 62 of the inflation fluid transfer conduit 64 in a fluid-tight, frictionally engaged manner. Likewise, to ensure proper attachment/operative connection of these components together, one or more conventional adhesive compounds (e.g. standard epoxy or cyanoacrylate materials) may be applied to the first end 62 of the conduit 64, the opening 96, or both of these components. Attachment can also be accomplished using conventional thermal welding techniques.

The embodiment of FIG. 5 may be employed in situations where, taking into consideration the materials being used to produce the apparatus 10 and the construction techniques of interest, it is desirable to have an "external" system for connecting the bladder member 46 to the supply of inflation fluid 72 retained within the delivery apparatus 74. In any event, the arrangement of components shown in FIG. 5 represents a further alternative system which may be employed to transfer fluid materials into and out of the apparatus 10, with this particular system likewise being applicable (if desired) to all of the other embodiments described herein including the embodiment of FIG. 4 and the additional systems which will now be described.

Referring back to FIG. 2, a number of further optional modifications to the apparatus 10 are also possible. These modifications are likewise applicable to the other embodiments of the apparatus 10 discussed herein. One system of interest, while optional in nature, provides numerous important benefits. The apparatus 10 shown in FIGS. 1–3 includes an electrical potential transmission system 100 passing through (e.g. "operatively connected") to the fluid transfer conduit 12 for receiving evoked or non-evoked electrical potentials from middle/inner ear tissues and transmitting them out of the ear for detection and analysis. Likewise, the electrical potential transmission system 100 may be employed to deliver electrical potentials to the middle/inner ear for treatment purposes regarding a number of conditions including but not limited to tinnitus. While the electrical potential transmission system 100 is shown in FIG. 2 as being "embedded" or molded within the side wall 30 of the fluid transfer conduit 12 (which is accomplished during the manufacturing process), it is important to note that the electrical potential transmission system 100 may be attached to the apparatus 10 in many different ways including but not limited to (1) attachment to the outer surface 32 of the side wall 30 associated with the fluid transfer conduit 12 using a conventional adhesive composition (e.g. standard epoxy resin or cyanoacrylate materials) wherein the electrical potential transmission system 100 (discussed in greater detail below) will pass through the central opening 84 in the main body portion 82 of the bladder member 46; and (2) passage through one or more of the passageways (e.g. "lumen") which are present within the fluid transfer conduit 12 including the main fluid flow passageway 22 or a separate, dedicated passageway sized to receive the system 100 (not shown). Accordingly, this embodiment of the present invention shall not be restricted to any particular positions or attachment techniques relative to the electrical potential transmission system 100, with all of the above-described methods being considered equivalent and encompassed within the term "operatively connected" relative to the fluid transfer conduit 12. However, for the sake of clarity, the following discussion shall involve placement of the electrical potential transmission system 100 directly within the side wall 30 of the fluid transfer conduit 12, with all of the information provided below being equally applicable to operative connection of the electrical potential transmission system 100 using the other procedures outlined above.

In a preferred embodiment, the electrical potential transmission system 100 consists of an elongate conductive member 102 fixedly positioned (e.g. molded) within the side wall 30 of the fluid transfer conduit 12 as illustrated (or attached using the other methods previously discussed). The elongate conductive member 102 may involve a variety of different structures. For example, it is preferred that the elongate conductive member 102 consist of a thin wire 104 (e.g. #27 gauge) manufactured from titanium, silver, platinum, or other highly conductive material. The wire 104 is preferably coated with a layer 106 of insulation thereon (FIG. 1) where the wire 104 is not embedded within the side wall 30 of the conduit 12. In other embodiments where, for example, the wire 104 is positioned outside of the conduit 12 and exteriorly attached thereto, the entire wire 104 is preferably coated with the layer 106 of insulation. Representative insulation materials suitable for this purpose include but are not limited to heat shrinkable Teflon® (polytetrafluoroethylene) tubing of a type that is well known in the art. The wire 104 further includes a proximal end 110 and a distal end 112 as illustrated (FIG. 2). It should also be noted that the elongate conductive member 102 may involve other structures equivalent to the wire 104. For example, a substantially flat, flexible metallic strip (not shown) may be used in place of the wire 104 (mounted either internally or externally relative to the fluid transfer conduit 12), although the wire 104 is preferred.

As illustrated in FIGS. 1–3, the proximal end 110 of the wire 104 preferably extends outwardly beyond the first end 14 of the conduit 12. In a preferred embodiment, the proximal end 110 of the wire 104 includes a conductive spherical member 114 (FIG. 1) secured thereto (e.g. integrally formed thereon). The spherical member 114 is optimally manufactured from the same material used to construct the wire 104 as outlined above. Use of the spherical member 114 facilitates direct contact between the wire 104 and the ear tissues of concern (e.g. the round window membrane or other desired structures). In an alternative embodiment (not shown), the proximal end 110 of the wire 104 may include a rounded club or hook-like portion thereon as shown in U.S. Pat. No. 5,421,818 to Arenberg or a loop, spoon, flat, or mushroom-shaped structure instead of the spherical member 114. Thus, the proximal end 110 of the wire 104 may encompass a variety of different forms, and shall not be restricted to any single structure or design. It should likewise be noted that, while the conductive member 102 (e.g. the wire 104) is primarily discussed herein as a means to receive electrical potentials, it may again be possible to use the conductive member 102 to apply electrical potentials to ear tissues of interest in order to (1) measure responsive stimuli therefrom; (2) treat the tissues using therapeutic electrical pulses; and/or (3) implement iontophoresis procedures. Thus, the conductive member 102/wire 104 of the claimed invention shall not be exclusively limited to the receipt of electrical potentials. In addition, the term "electrical potential" as used herein shall be broadly construed to encompass any type of electrical signal, current, voltage, or impulse regardless of form, magnitude, or origin.

The distal end 112 of the wire 104 preferably extends outwardly beyond the second end 16 of the fluid transfer conduit 12 as illustrated in FIG. 2. Upon insertion of the apparatus 10 into the middle ear of a patient, the distal end 112 of the wire 104 will pass through the incised tympanic membrane (or beneath a surgically formed tympanomeatal flap as outlined below), through the external auditory canal of the patient, and will ultimately extend outwardly from the patient's ear. The distal end 112 (if desired) is then readily connected to an external monitoring apparatus 120 (FIG. 8) of conventional design which collects and characterizes resting or evoked electrical potentials ultimately received from the inner ear. Further information concerning the monitoring apparatus 120 will be presented below.

As previously noted, the conductive member 102/wire 104 is especially designed to receive electrical potentials which originate within selected inner ear tissues. This capability is particularly useful in connection with a process known as "ECoG" which is an abbreviation for "electrocochleography". Electrocochleography is a known technique for measuring electrical potentials from the inner ear which basically involves measurement of the whole nerve-cochlear action potential (hereinafter "AP"). Alternatively, ECoG can be employed to indirectly measure hair cell electrical activity. ECoG can also be used to measure the summating potential (hereinafter "SP") within the inner ear in response to externally generated clicks, tone bursts, and/or pips. The SP is basically a D.C. distortion potential which can indicate the amount of distortion in the cochlear duct associated with endolymphatic hydrops or other changes in the inner ear. The relative amount of distortion may be expressed either as an SP/AP ratio (in response to externally-generated clicks, etc.), or as an absolute measurement in response to specific, externally-generated tone bursts and the like. Cochlear microphonics can also be measured as well as otoacoustic emissions (hereinafter "OAE") in order to assess hair cell function or dysfunction. Finally, endocochlear potentials can be measured using the components described herein if selected portions of the conductive member 102 are operatively positioned within the cochlea rather than outside of the cochlea. Further information on ECoG is presented in Portmann, M., "Electrophysiological correlates of endolymphatic hypertension and endolymphatic hydrops: an overview of electrocochleography (ECoG)", Proceedings of the Third International Symposium and Workshops on the Surgery of the Inner Ear, Snowmass, Colo. (USA) Jul. 29–Aug. 4, 1990 as reported in *Inner Ear Surgery*, edited by I. Kaufman Arenberg, Kugler Publications, Amsterdam/New York, pp. 241–247 (1991) and in U.S. Pat. No. 5,421,818 to Arenberg which are both incorporated herein by reference. The elongate conductive member 102/wire 104 may also be employed in connection with iontophoresis techniques as defined above.

Accordingly, the elongate conductive member 102 (e.g. wire 104) is especially useful in the implementation of conventional ECoG procedures. Resting or evoked electrical potentials received by the wire 104 through direct contact of the proximal end 110 (e.g. the spherical member 114) with selected ear tissues are routed through the wire 104 to the distal end 112 which is operatively connected (using conventional electrical connecting clips and the like) to the monitoring apparatus 120 as stated above and particularly shown in FIG. 8. An exemplary monitoring apparatus 120 suitable for use herein consists of commercially available ECoG detection systems sold under the names "Viking II™" and "Spirit™" by Nicolet, Inc. of Madison, Wis. (USA). However, a variety of different commercial systems may be employed to receive and quantify electrical potentials from the conductive member 102/wire 104, including but not limited to computer-monitored voltage amplifier/analog-to-digital converter units known in the art. As noted above, the wire 104 is sufficiently long to enable the distal end 112 thereof to terminate at a position outside of the patient's ear. In this manner, attachment of the distal end 112 of the wire 104 to the monitoring apparatus 120 is greatly facilitated. Dimensional information regarding the elongate conductive member 102/wire 104 will be provided below.

Use of the elongate conductive member 102/wire 104 provides a number of important benefits including those related to ECoG and iontophoresis techniques as discussed above. While the elongate conductive member 102 shall be considered an optional element in connection with the apparatus 10, it may nonetheless be used (if desired in accordance with preliminary pilot studies) on any or all of the various embodiments outlined herein. For example, the elongate conductive member 102 is used in the embodiments of FIGS. 1–4 and 6–7, but not in the embodiment of FIG. 5 (which could likewise include the conductive member 102 if desired). Thus, the information provided above concerning use of the elongate conductive member 102 in connection with the embodiment of FIGS. 1–3 is equally applicable to the other embodiments of the invention, with the foregoing discussion being incorporated by reference relative to such other embodiments.

Another optional feature of the claimed system is illustrated in FIG. 5. Again, this particular feature of the invention is presented in FIG. 5 for the sake of clarity and is equally applicable (if desired) to all of the other embodiments discussed herein. With continued reference to FIG. 5, the open first end 14 of the fluid transfer conduit 12 further includes a semi-permeable membrane 130 attached thereto. Specifically, the semi-permeable membrane 130 is secured to the first end 14 of the conduit 12 so that it is located directly over and in front of the fluid flow passageway 22. Attachment of these components is optimally accomplished by using a selected adhesive (e.g. an epoxy or cyanoacrylate compound known in the art) which is applied to the inner surface 132 of the membrane 130, the first end 14 of the conduit 12, or both components. While FIG. 5 illustrates operative attachment of the semi-permeable membrane 130 to the first end 14 of conduit 12, the membrane 130 may be placed in a variety of other positions as long as it is able to at least partially block the passageway of interest (including but not limited to the fluid flow passageway 22) so that any fluid materials to be transferred through the passageway will first need to pass through the membrane 130. The term "operatively attached" as used herein relative to the semi-permeable membrane 130 shall involve a situation in which the membrane 130 is attached in any manner (1) directly to and over the open first end 14 and/or open second end 16 of the fluid transfer conduit 12; or (2) inside the passageway(s) through the conduit 12 (e.g. fluid flow passageway 22) at any location therein but optimally adjacent the first end 14 or second end 16 using the attachment methods listed above.

Many different materials may be employed in connection with the semi-permeable membrane 130 without limitation including a variety of proprietary commercial products. Representative semi-permeable membranes 130 which may be used in accordance with this embodiment involve commercially available materials produced from a wide variety of porous compositions including but not limited to cellulose acetate, polytetrafluoroethylene, polycarbonate, polyacrylonitrile, polyethylenimine, cellulose diester, cellulose ether, and cellulose acylate. From a general standpoint, the term "semipermeable membrane" as used herein shall be defined to involve a structure which is selectively permeable to molecules of varying size and/or charge (depending on the membrane compositions under consideration) and will permit certain materials to pass therethrough while preventing others from passing (or allowing them to pass slowly or to only pass upon the modification of various environmental conditions including temperature, pH, and the like). The semi-permeable membrane 130 is specifically designed to allow fluid materials being transferred through the fluid transfer conduit 12 to pass into or out of the conduit 12 in a more controlled, slower, and uniform manner when desired (e.g. in the case of drug microdosing and similar situations.) Other uses associated with the semi-permeable membrane 130 include but are not limited to the limitation of fluid flow into the desired fluid-receiving zone so that only drug molecules of a selected size (as determined be preliminary studies) can enter the zone. In a preferred embodiment as shown in FIG. 5, the semi-permeable membrane 130 is attached to the end of the fluid transfer conduit 12 (e.g. first end 14) that ultimately resides within the fluid-receiving zone between the inflated bladder member 46 (or bladder member 86) and the round window niche (regardless of whether the fluid-receiving zone is sealed or unsealed). As previously noted, the use of a semi-permeable membrane 130 in connection with the fluid transfer conduit 12 is optional and shall be employed in accordance with preliminary pilot testing. The semi-permeable membrane 130 (which is shown in enlarged schematic format for the sake of clarity in FIG. 5) will typically have a thickness "$T_2$" of about 0.0001–0.1 mm. Also, in embodiments where the elongate conductive member 102/wire 104 is employed, the membrane 130 should be placed in a position which will avoid any need to pass the member 102/wire 104 through the membrane 130 (although passage of the member 102/wire 104 through the membrane 130 may be undertaken if needed).

Next, the specific sub-system which may be used to transfer fluid materials (preferably liquids and, in certain cases, gels or gases/vapors) into and out of the various embodiments of the apparatus 10 will be discussed in detail. The terms "transfer", "transferring", or "transferred" shall encompass, without limitation, the movement of fluid materials in either direction within the fluid transfer conduit 12 (e.g. either toward or away from the middle ear structures of concern including the round window niche/round window membrane.) For example, these terms may involve the delivery of one or more therapeutic fluid compositions into and through the internal passageway(s) of the fluid transfer conduit 12 (including the fluid flow passageway 22) by a selected delivery system. The therapeutic fluid compositions will then enter the fluid-receiving zone within the round window niche and come in contact with the round window membrane. Accordingly, the terms listed above may have a number of different meanings, all of which involve the relative movement of fluid materials through the fluid transfer conduit 12 for a variety of purposes, regardless of the number of internal passageways which are used within the conduit 12.

With particular reference to FIG. 8, an exemplary subsystem which may be used to transfer fluid materials into and out of the various embodiments of the apparatus 10 is schematically illustrated. While the system in FIG. 8 is shown in connection with the embodiment of FIG. 2, it is likewise applicable to all of the other embodiments described herein. The distal end 26 of the fluid flow passageway 22 associated with the conduit 12 (FIG. 2) is operatively connected to the first end 134 of a tubular conduit 136 (FIG. 8). Attachment of these components may be accomplished in a number of conventional ways including the use of standard adhesive materials (e.g. cyanoacrylate or epoxy adhesives and the like), frictional engagement, thermal welding, or a combination of these techniques. The conduit 136 terminates at a second end 140 that is remotely spaced from the first end 134 (and is preferably located outside the ear of the living subject being treated). The conduit 136 (which is optimally produced from the same materials listed above in connection with the fluid transfer conduit 12) likewise includes at least one internal passageway 142 which extends continuously through the conduit 136 from the first end 134 to the second end 140. The second end 140 of the conduit 136 is preferably attached to a supply of therapeutic fluid 144 which resides within a selected fluid transfer device 146. The present invention shall not be restricted to any particular type of fluid transfer device 146 provided that the device 146 is capable of delivering the therapeutic fluid 144 into the fluid transfer conduit 12 of the apparatus 10 in a rapid and effective manner. Representative systems which may be employed in connection with the fluid transfer device 146 include, without limitation, conventional hypodermic syringe systems, micro-pumps, and other equivalent fluid transfer units. For example, the fluid transfer device 146 may involve a standard needle-type syringe apparatus as shown and described in U.S. Pat. No. 5,421,818 or other systems including but not limited to a product which is known as an "osmotic pump." Such a pump is described in Kingma, G. G., et al., "Chronic drug infusion into the scala tympani of the guinea pig cochlea", *Journal of Neuroscience Methods*, 45:127–134 (1992) which is incorporated herein by reference. An exemplary, commercially available osmotic pump may be obtained from the Alza Corp. of Palo Alto, Calif. (USA) and is generally described in U.S. Pat. Nos. 4,320,758 and 4,976,966. However, it should again be emphasized that the present invention shall not be limited to any particular type of fluid transfer system (s). In fact, other comparable fluid transfer devices may be used in connection with all embodiments of the claimed invention.

The selected fluid transfer device 146 employed in connection with the apparatus 10 should also preferably be capable of withdrawing any residual fluid materials through the fluid transfer conduit 12 from the middle ear (particularly the round window niche) as discussed below. The withdrawal process will typically take place instead of or after delivery of the therapeutic fluid 144. Fluid withdrawal will take place if needed and desired in accordance with clinical investigations and the need to implement dialysis techniques. Likewise, an additional separate fluid transfer device of the type discussed above (not shown) may also be operatively connected to the second end 140 of the conduit 136 for fluid withdrawal purposes. The connection of multiple fluid transfer devices to the second end 140 can be achieved using conventional attachment hardware (including standard "Y"-type connection joints). Only one fluid transfer device 146 is illustrated in FIG. 8 for the sake of clarity.

The term "residual fluid materials" as used above can include a number of different products ranging from excess therapeutic fluids 144 that were not completely delivered to the desired target tissues (including the round window niche) to tissue fluid materials originating from within the inner ear. These tissue fluids could include those which diffused across the round window membrane from the inner ear into the round window niche. All of the specific systems listed above in connection with the fluid transfer device 146 will have both fluid delivery and extraction capabilities, and can therefore be used for both purposes. However, in a preferred embodiment, the selected fluid transfer device 146 should be capable of delivering or withdrawing fluid materials to and from the fluid transfer conduit 12 at a rate of at least about 0.0001–0.1 cc per hour, with this value being presented in a non-limiting manner for example purposes. In addition, to properly deliver and/or withdraw fluid materials from the apparatus 10, the conduit 136 may include an optional in-line control valve schematically illustrated in FIG. 8 at reference number 150. The valve 150 (which is typically of a conventional rotary, ball, or other type) may be positioned in-line within the conduit 136 or can be integrated directly into the fluid transfer device 146 or fluid flow passageway 22, depending on the type of device 146 under consideration. Use of the valve 150 is optional as previously indicated and shall be selected for use in accordance with preliminary pilot studies on the particular fluid transfer system under consideration. Nonetheless, for the purposes of this invention and in accordance with the information provided below, the conduit 136, fluid transfer device 146, and valve 150 (if used) shall collectively be designated herein as a "fluid transfer system 152" (FIG. 8). As a final note, it should be emphasized that the present invention (including all of its various embodiments) shall not be restricted to any particular systems or sub-systems for introducing or removing fluid materials from the apparatus 10, with a number of different devices being capable of performing this function. Thus, the representative systems which are shown and described herein are presented for example purposes only and are non-limiting.

Figure 6:
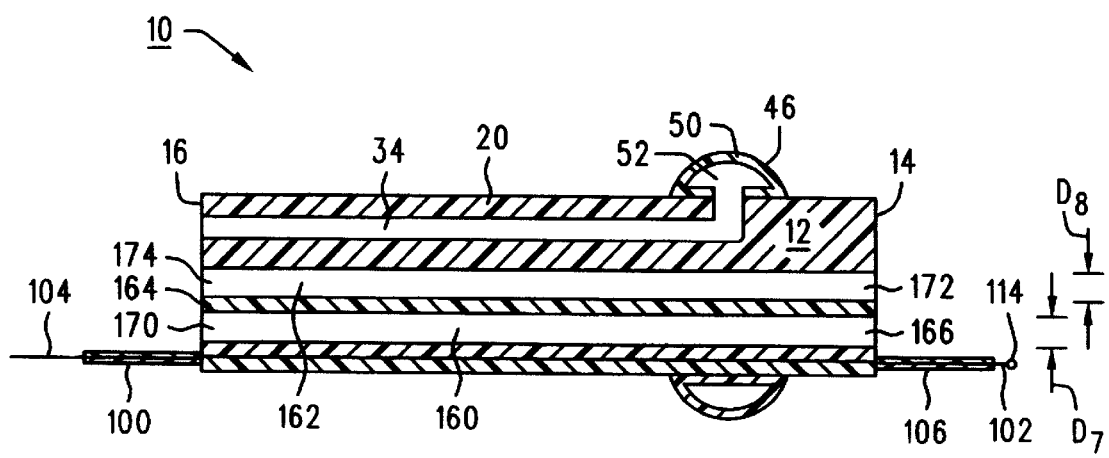
FIG. 6 is a cross-sectional view in enlarged format of a still further alternative embodiment of the apparatus of FIGS. 1–2 which includes an additional fluid flow passageway therein so that fluid materials being transferred to the ear of a patient can be maintained separately from any fluid materials being extracted from the patient, with the bladder member being shown in an inflated state.

A further embodiment of the invention is illustrated schematically in FIG. 6 and will now be discussed. All of the components, materials, construction materials, dimensions, and other parameters listed above in connection with the embodiment of FIG. 2 are equally applicable to the embodiment of FIG. 6 unless otherwise indicated herein. Accordingly, the discussion presented above regarding the apparatus 10 shown in FIG. 2 is incorporated by reference relative to the embodiment of FIG. 6. As shown in FIG. 6, the apparatus 10 again includes all of the components associated with the embodiment of FIG. 2, except for the addition of various items which will now be summarized. Basically, in the embodiment of FIG. 6, the fluid flow passageway 22 presented in FIG. 2 is recharacterized in FIG. 6 as a fluid delivery passageway 160 which is exclusively used to deliver fluid materials (including the selected therapeutic fluid 144 [FIG. 8]) to the desired ear tissues including the round window niche/round window membrane. For fluid extraction purposes including the removal of "residual fluid materials" as defined above, a separate fluid extraction passageway 162 is provided adjacent the fluid delivery passageway 160. Both of the passageways 160, 162 are completely separated from each other so that the cross-contamination of fluid materials travelling through them is prevented. To accomplish separation, an uninterrupted barrier wall 164 is provided between both of the passageways 160, 162.

Each of the passageways 160, 162 are preferably equal in size and diameter. Specifically, the fluid delivery passageway 160 will have a representative, non-limiting uniform diameter "$D_7$" of about 0.05–0.75 mm, with the fluid extraction passageway 162 having an exemplary and equivalent diameter "$D_8$" of about 0.05–0.75 mm (FIG. 6). Regarding the overall diameter of the fluid transfer conduit 12, it will typically be substantially the same as the diameter "$D_1$" of the conduit 12 shown in FIG. 2. Furthermore, the fluid delivery passageway 160 has a proximal end 166 and a distal end 170, while the fluid extraction passageway 162 also has a proximal end 172 and a distal end 174 (FIG. 6).

As previously noted, the use of a multiple-passageway version of the claimed apparatus 10 is again particularly important in situations where cross-contamination between (1) the fluid materials being delivered into the ear; and (2) the residual fluid materials being removed or exchanged is not desired. This can be important in situations where therapeutic agents (e.g. drugs) need to be delivered in very precise (e.g. microgram, microliter, or nanoliter) amounts over controlled time periods. Furthermore, the apparatus of FIG. 6 may also be employed in situations involving the dialysis of fluids in connection with a designated treatment program. The system illustrated in FIG. 6 may be used in connection with all of the various bladder designs listed herein in order to provide either a partially or completely sealed fluid-receiving zone. The multi-passageway conduit 12 of FIG. 6 may likewise include (1) the semi-permeable membrane 130 shown in FIG. 5; and/or (2) the elongate conductive member 102 which is, in fact, illustrated in FIG. 6. The present invention shall likewise not be restricted regarding the number of fluid delivery or fluid extraction passageways employed within the fluid transfer conduit 12, with many different multiples of these elements being possible (including those which employ two or more passageways or at least one conductive member). Furthermore, the fluid delivery passageway 160 and the fluid extraction passageway 162 will each typically have a fluid transfer system operatively connected thereto (not shown) of the same type illustrated in FIG. 8 at reference number 152 (which includes the conduit 136, fluid transfer device 146, and optional valve 150). Specifically, a separate fluid transfer system 152 may be attached to the distal end 170 of the fluid delivery passageway 160 and the distal end 174 of the fluid extraction passageway 162. In an alternative embodiment, a single fluid transfer system 152 may be connected to both of the distal ends 170, 174 of the passageways 160, 162 if desired, with such a system involving alternating operation of the single fluid transfer system 152 as needed. All of the representative fluid transfer devices 146 which were previously discussed relative to the system of FIG. 2 (including hypodermic syringes, pump units, and the like) can be used in the embodiment of FIG. 6. Accordingly, the apparatus of FIG. 6 shall not be restricted to the use of any particular sub-system(s) for fluid delivery/extraction. In a non-limiting example involving separate fluid transfer systems 152 associated with each passageway 160, 162, the fluid transfer device 146 operatively connected to the fluid delivery passageway 160 may consist of an osmotic pump as described above, while the fluid transfer device 146 employed in connection with the fluid extraction passageway 162 may involve a hypodermic syringe unit. As will become readily apparent from the next section of this discussion, the systems described herein all function in a similar manner regardless of the number of internal passageways which are used. In particular, all of the various embodiments shown in FIGS. 1–9 incorporate a common group of features, namely, at least one fluid transfer conduit with one or more passageways therethrough having an inflatable bladder member operatively connected to the conduit. This design permits the claimed apparatus 10 to be inserted and retained within the round window niche of a patient (or other internal ear cavity) in a secure, unique, and minimally-invasive manner. Likewise, in view of the common features and attributes associated with the embodiments shown in FIGS. 1–9, they have all been designated with the reference number 10.

Figure 7:
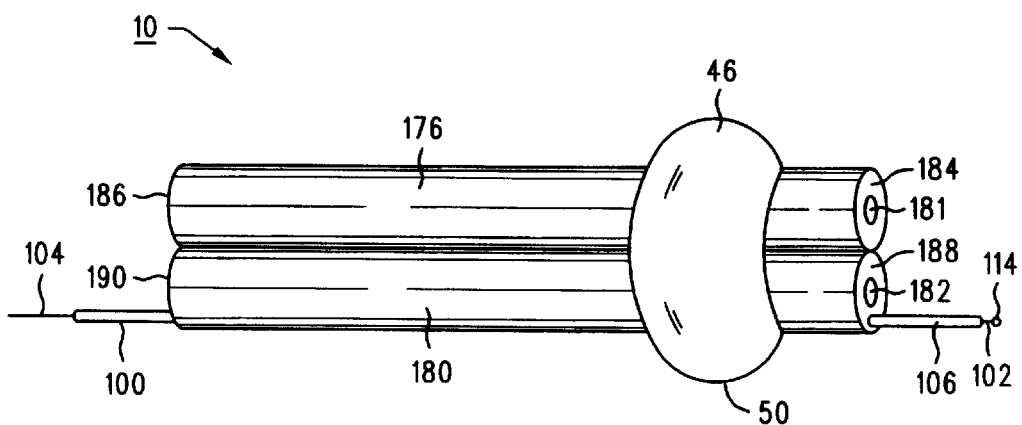
FIG. 7 is a front perspective view in enlarged format of a still further alternative embodiment of the apparatus of FIGS. 1–2 which incorporates separate (e.g. individual) conduits for the delivery and extraction of fluid materials from the ear of a patient, with the bladder member being shown in an inflated state.

As discussed above, the primary embodiments of the claimed invention involve the use of a single fluid transfer conduit 12 having one or more internal passageways therethrough. However, in addition to this single-conduit embodiment (which is preferred), an alternative apparatus 10 may also be employed which includes multiple fluid transfer conduits (e.g. a fluid extraction conduit 176 and a fluid delivery conduit 180) each having the inflatable bladder member 46 operatively connected thereto (FIG. 7). Both of the conduits 176, 180 discussed in this embodiment are optimally equivalent to each other in structure, size, and internal/external configuration. Likewise, the conduits 176 and 180 will have at least one or more internal passageways therethrough. As shown in FIG. 7, conduit 176 includes passageway 181 while conduit 180 contains passageway 182. Conduit 180 likewise includes the elongate conductive member 102/wire 104 therein as discussed above relative to the fluid transfer conduit 12, although this item may also be present within the conduit 176. Regarding the diameters associated with the conduits 176, 180 (and passageways 181, 182), they will (in a preferred embodiment) be approximately 50% of the values listed above in connection with the fluid transfer conduit 12/passageway 22 although such values may be varied as needed. All of the other information presented herein regarding the embodiment of FIGS. 1–2 is incorporated by reference in the embodiment of FIG. 7. The only substantial difference between the embodiment of FIGS. 1–2 and the embodiment of FIG. 7 is the use of multiple conduits 176, 180. It should also be noted that the conduit 176 includes an open first end 184 and an open second end 186, while the conduit 180 has an open first end 188 and an open second end 190. Likewise, either or both of the multiple conduits 176, 180 in the embodiment of FIG. 7 can include the optional components listed above, namely, (1) the semi-permeable membrane 130 shown in FIG. 5; and/or (2) the elongate conductive member 102/wire 104.

In accordance with the multiple conduit design of FIG. 7, cross-contamination of the fluid materials being transferred through the apparatus 10 is avoided which can be important in situations where therapeutic agents (e.g. drugs) need to be delivered in very precise (e.g. microgram, microliter, or nanoliter) amounts over controlled time periods. In a multi-conduit system of the type described above, each of the conduits 176, 180 will typically have a fluid transfer system operatively connected thereto (not shown) of the same type shown in FIG. 8 at reference number 152 (which includes the conduit 136, fluid transfer device 146, and optional valve 150). Specifically, a separate fluid transfer system 152 may be attached to the second end 186 of the fluid extraction conduit 176 and the second end 190 of the fluid delivery conduit 180. In an alternative embodiment, a single fluid transfer system 152 may be connected to both of the conduits 176, 180 if desired, with such a system involving alternating operation of the single fluid transfer system 152 as needed. All of the representative fluid transfer devices 146 which were previously discussed relative to the system of FIG. 2 (including hypodermic syringes, pump units, and the like) can be used in the embodiment of FIG. 7. Accordingly, the apparatus of FIG. 7 shall not be restricted to any particular sub-system(s) for fluid delivery/extraction. In a non-limiting example involving separate fluid transfer systems 152 associated with each conduit 176, 180, the fluid transfer device 146 operatively connected to the fluid extraction conduit 176 may consist of a hypodermic unit as discussed above, while the fluid transfer device 146 employed in connection with the fluid delivery conduit 180 may involve an osmotic pump. Again, many different combinations of fluid transfer devices 146 can be utilized in connection with this embodiment of the invention which shall not be restricted to any given component configurations.

Finally, the present invention shall not be limited to any numerical parameters relative to the devices described above which may be varied as needed in accordance with the particular living subject involved and other factors as determined by preliminary routine testing. By way of example and with reference to FIG. 2, some exemplary dimensions are illustrated which are applicable to all of the other embodiments presented herein. Specifically, as shown in FIG. 2, the fluid transfer conduit 12 (after the bladder member 46 is attached thereto) will be divided into a primary section 192 and a secondary section 194. In a representative and non-limiting embodiment, the primary section 192 (and the first end 14) of the conduit 12 will extend outwardly ahead of the bladder member 46. As a result, during use of the apparatus 10, the primary section 192 and first end 14 will be located entirely within the round window niche (or other internal ear cavity) of the subject being treated. Alternatively, the conduit 12 may not extend outwardly from the bladder member 46 and will be flush therewith. To achieve proper use of the apparatus 10 shown in FIG. 2, the primary section 192 of the fluid transfer conduit 12 will have a representative length "$L_1$" (FIG. 2) of about 0–3 mm, although this value may be varied as needed and desired. The conduit 12 will also include a secondary section 194 as previously noted which (along with the second end 16 of the conduit 12) is positioned behind the bladder member 46. As a result, during use of the apparatus 10, the secondary section 194 and second end 16 of the conduit 12 will be located entirely outside of the round window niche (or other internal ear cavity of interest) and at least partially within the external auditory canal of the patient. To achieve proper use of the apparatus 10, the secondary section 194 will have a representative length "$L_2$" of about 20–180 mm although this value may again be varied as needed and desired. Furthermore, the length "$L_3$" of the bladder member 46 (and bladder member 86 in the embodiment of FIG. 5) will optimally be about 1–5 mm. Taking all of these values into consideration, the overall length "$L_4$" of the entire apparatus 10 (e.g. the fluid transfer conduit 12) will be about 21–188 mm.

With continued reference to FIG. 2, some representative dimensions associated with the elongate conductive member 102/wire 104 will now be provided. In a preferred and optimum embodiment, the total length "$L_5$" of the wire 104 from the proximal end 110 to the distal end 112 (measured when straight) will be about 41–339 mm. Likewise, in the representative, non-limiting system 10 of FIG. 2, the sections of the wire 104 which are not embedded within the side wall 30 of the fluid transfer conduit 12 may be divided into two portions, namely, a first portion 196 and a second portion 198. The first portion 196 (which is ultimately positioned within the fluid-receiving zone inside the round window niche or other cavity as discussed below) will typically have a length "$L_6$" (FIG. 2) of about 0–1 mm. Likewise, the second portion 198 (which is ultimately located within the external auditory canal of a patient) will normally have a length "$L_7$" (FIG. 2) of about 20–150 mm. The section of the wire 104 which is embedded within the side wall 30 of the fluid transfer conduit 12 (which does not need to be covered with the layer of insulation 106 as shown in FIG. 2) will have a representative length "$L_8$" of about 21–188 mm which is substantially equal to the length "$L_4$" of the conduit 12 as previously indicated. The length of the entire wire 104 (e.g. the insulated and non-insulated sections) may be longer or shorter than the values listed above if needed, and sufficiently long to extend outwardly from the patient's ear. All of the above parameters may again be modified as necessary in accordance with a variety of factors as determined by pre-treatment testing on the patient of concern and are provided for example purposes only.

B. Methods of Use

Methods for using the devices associated with the claimed fluid transfer and diagnostic systems will now be discussed. This section will be primarily directed to insertion of the devices into the middle ear/round window niche of a subject, but will not be exclusively limited to this environment. The present invention shall likewise not be restricted to any particular surgical methods for introducing the devices of the invention into a living subject's ear, with many different techniques being suitable for this purpose provided that, in some manner, the fluid receiving zone ("fluid transfer space") of the invention is effectively created. Furthermore, the structures of the human ear illustrated in FIGS. 8 are schematic in nature and enlarged for the sake of clarity. More detailed information concerning these structures is provided in U.S. Pat. No. 5,421,818 which is incorporated herein by reference. It is also important to emphasize that, while the apparatus 10 associated with the embodiment of FIGS. 1–2 will be the subject of the following discussion, the methods described herein are equally applicable to all of the embodiments listed above (including those presented in the other drawing figures, namely, FIGS. 3–7). The selection of the embodiment of FIGS. 1–2 for inclusion in the drawing of FIG. 8 shall therefore not be regarded as limiting.

FIG. 8 is a schematic, partial cross-sectional view of the ear 200 of a human subject illustrating the treatment apparatus 10 of FIGS. 1–2 inserted therein. As shown in FIG. 8, the apparatus 10 of FIGS. 1–2 is positioned so that the bladder member 46 is entirely located within the middle ear, generally designated in FIG. 8 at reference number 202. The inner ear is shown at reference number 204, with the specific components of the inner ear 204 (including the cochlea, the endolymphatic sac, and the endolymphatic duct being omitted for the sake of clarity and illustrated in U.S. Pat, No. 5,421,818). The round window membrane is generally designated at reference number 206, and constitutes an interface tissue structure between the middle ear 202 and the inner ear 204. Likewise, the round window niche is shown at reference number 210 (which basically consists of an internal cavity 212), with the round window niche 210 further including an interior side wall 214 and a main opening 216 leading into the internal cavity 212/round window niche 210.

The first step in using the apparatus 10 involves insertion of the bladder member 46 (optimally in an uninflated state)

within the middle ear 202 as illustrated. The bladder member 46 is then physically urged into the main opening 216 leading into the round window niche 210 so that the bladder member 46 is inserted into the niche 210. Once the bladder member 46 is positioned within the round window niche 210 in the subject, it is thereafter inflated in accordance with the parameters and techniques listed above in the previous section of this discussion. FIG. 8 illustrates the bladder member 46 prior to inflation.

Figure 9:
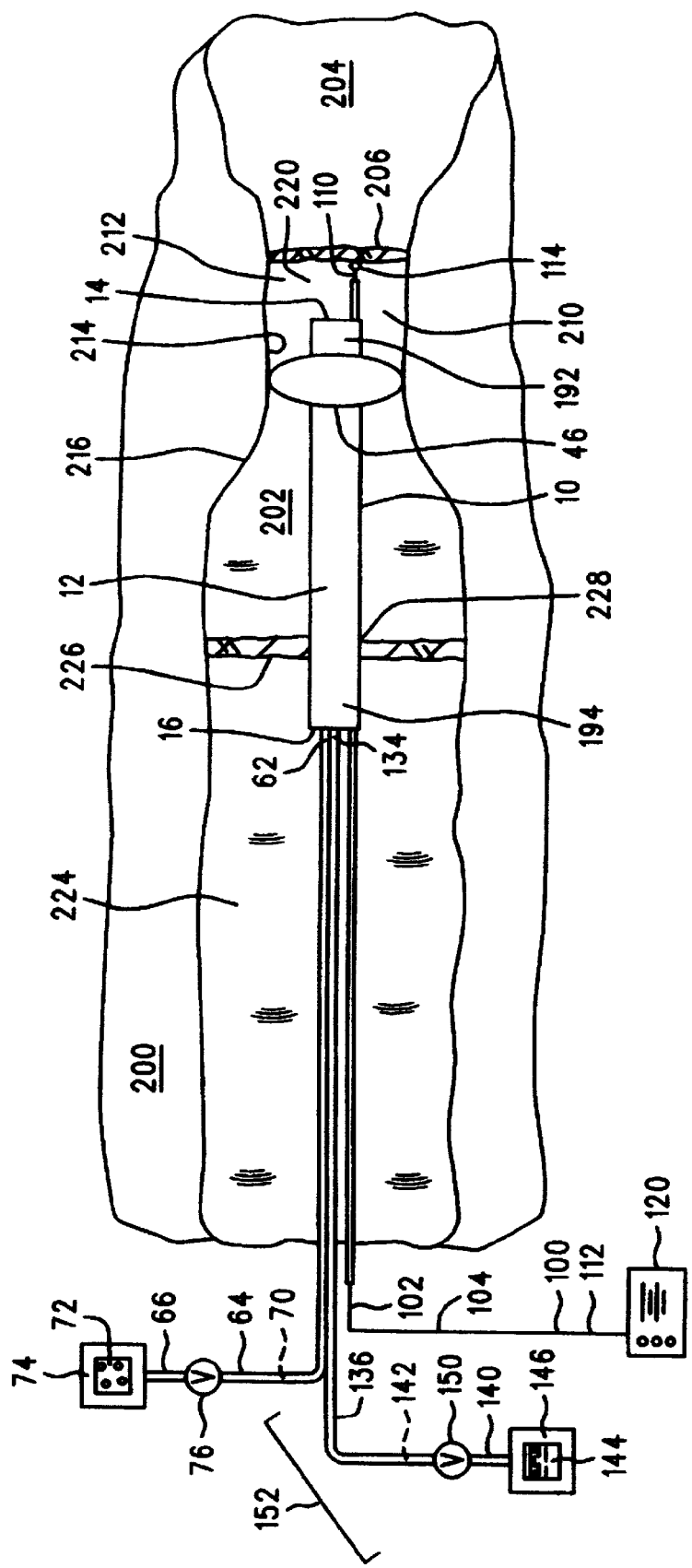
FIG. 9 is a schematic representation of the fluid transfer and diagnostic apparatus of FIGS. 1–2 positioned within the ear of a human subject after inflation of the bladder member.

To inflate the bladder member 46, the delivery apparatus 74 (which consists of a hypodermic syringe, pump, or the like) is initially activated in order to transfer the inflation fluid 72 (e.g. air or other fluid) through the inflation fluid transfer conduit 64, valve 76 (if used), and into the inflation fluid transfer passageway 34 (FIG. 2) of the fluid transfer conduit 12. The inflation fluid 72 then enters the internal cavity 52 within the bladder member 46. In accordance with the resilient character of the outer wall 50 of the bladder member 46, the bladder member 46 will expand, thereby engaging the interior side wall 214 of the round window niche 210 (FIG. 9). As a result, a seal is created by the bladder member 46 in accordance with its annular character as discussed above to define a sealed fluid-receiving zone 220 or "inner ear fluid transfer space" which is shown in FIG. 9 The fluid-receiving zone 220 is bounded by (1) the bladder member 46 which forms a first boundary; and (2) the round window membrane 206 which forms a second boundary. Incidentally, inflation of the bladder member 46 will be undertaken using substantially the same procedures regardless of whether the embodiment of FIG. 2 or FIG. 5 is employed.

The bladder member 46 is primarily maintained in position within the round window niche 210 by frictional engagement between the bladder member 46 and the interior side wall 214 of the niche 210. However, in certain cases as determined by routine clinical investigation, small amounts of adhesive materials may be employed which would be applied to and between the bladder member 46 and the interior side wall 214 of the round window niche 210. Many different adhesive compounds (not shown) may be used for this purpose, with the present invention not being restricted to any particular chemical compositions. For example, autologous fibrin glue as described in U.S. Pat. No. 4,874,368 to Miller et al. (which is incorporated herein by reference) or other conventional medical grade adhesives may be employed. It is important to emphasize that the use of adhesive materials for this purpose is not normally required and will be employed only in exceptional situations.

The operational steps outlined above will likewise occur in connection with non-annular bladder systems including the substantially U-shaped bladder member 86 illustrated in FIG. 4. The only difference between this type of system and the interaction of components shown in FIGS. 8–9 is the creation of a non-sealed fluid-receiving zone 220 when bladder member 86 is employed, with fluid materials being permitted to "escape" through the open region 92 associated with the bladder member 86.

Once the bladder member 46 is in position as illustrated in FIG. 9, the primary section 192 of the fluid transfer conduit 12 (e.g. the first end 14) will be oriented within the round window niche 210 so that it is directly ahead of and adjacent to the round window membrane 206. This orientation is achieved by proper manipulation of the apparatus 10 in the patient being treated, and is likewise accomplished in accordance with the size parameters associated with the apparatus 10 as listed above. In this manner, fluid materials can be delivered to and withdrawn from the round window niche 210/fluid-receiving zone 220. Such an approach is likewise useful in connection with desired dialysis procedures relative to the inner ear 204.

With respect to the remaining portions of the apparatus 10, the secondary section 194 of the fluid transfer conduit 12 is at least partially positioned within (1) the middle ear 202; and (2) the external auditory canal 224. This orientation may again be accomplished in many ways. For example, as represented in FIG. 9, the fluid transfer conduit 12 (as well as other elements of the apparatus 10) pass through the tympanic membrane 226 which preferably has an incision 228 therein that allows the movement of these components therethrough. The conduit 12 may alternatively pass beneath a tympanomeatal flap (not shown) depending on the techniques chosen by the surgeon. It should likewise be noted that proper orientation of the apparatus 10 within a patient may be accomplished through the use of a conventional operating microscope or otologic endoscope apparatus of the type disclosed in U.S. Pat. No. 5,419,312 to Arenberg et al.

At this point, it is again important to emphasize that the present invention shall not be limited to (1) any methods for placement of the apparatus 10 in position within the ear 200; and (2) any particular orientation in connection with the apparatus 10 provided that the bladder member 46 effectively engages the interior side wall 214 of the round window niche 210 to create the fluid-receiving zone 220 or "fluid transfer space". In addition, packing materials of the type normally used for medical applications can be employed within the ear 200 to further secure/anchor the apparatus 10 in its desired location.

To use the apparatus 10 to deliver (e.g. transfer) a selected fluid material (including one or more therapeutic fluid compositions) into the fluid-receiving zone 220 within the round window niche 210 (FIG. 9), the fluid transfer device 146 discussed above is activated. Many different systems may again be used in connection with the fluid transfer device 146 as previously indicated. For example, the fluid transfer device 146 may involve a standard needle-type syringe apparatus (as disclosed in U.S. Pat. No. 5,421,818) or other systems including but not limited to osmotic pumps which are described above.

Upon activation of the fluid transfer device 146 (which contains a supply of a selected therapeutic fluid composition 144), the therapeutic fluid composition 144 then passes through the central passageway 142 of the conduit 136 (and valve 150 if used) and through the fluid flow passageway 22 in the fluid transfer conduit 12 (FIG. 2). The composition 144 thereafter passes out of the open first end 14 of the conduit 12, through the semi-permeable membrane 130 (if used—not shown in FIGS. 8–9), and into the fluid-receiving zone 220. Once the therapeutic fluid composition 144 is within the fluid-receiving zone 220, it can then diffuse through the round window membrane 206 and into the inner ear 204 for the treatment of tissues, fluids, fluid compartments, and tissue regions therein. Passage of the therapeutic fluid composition 144 through the round window membrane 206 takes place in accordance with the unique permeable character of this structure as discussed in detail above and in U.S. Pat. No. 5,421,818. Likewise, under certain circumstances, the fluid composition 144 can actually draw other fluid materials out of the inner ear 204 across the round window membrane 206 by osmosis and/or other forces.

It should also be noted that the term "transfer" may again involve the withdrawal of fluid materials from the fluid-receiving zone 220 (including "residual fluid materials"). The term "residual fluid materials" is defined above and can encompass many different products ranging from excess therapeutic fluid compositions 144 to fluid materials which passed across the round window membrane 206 from the inner ear 204. This step is accomplished in the embodiment of FIG. 8 by reversing the operation of the selected fluid transfer device 146 (e.g. syringe, pump, and the like) in order to exert suction force on the apparatus 10. As a result, the fluid materials of interest which reside within the fluid-receiving zone 220 are drawn into the first end 14 of the fluid transfer conduit 12 (including passage through the semi-permeable membrane 130 if used—not shown in FIGS. 8–9). The fluid materials then pass through the fluid flow passageway 22 in the conduit 12, through the conduit 136, valve 150 (if used), and into the fluid transfer device 146 for analysis, disposal, and the like. In this manner, residual or other fluid materials may be effectively removed from the fluid-receiving zone 220. It should likewise be added that the fluid transfer device 146 can be operated at any desired intervals including rapid, successive use thereof to achieve a "flushing" of fluid materials into and out of the ear 200. The amount of materials to be delivered and withdrawn from the ear 200 may vary, depending on the clinical diagnosis of the treating physician, with the present invention not being restricted to any particular fluid quantities. Furthermore, as previously stated, separate fluid transfer devices 146 can be operatively connected to the apparatus 10 for fluid delivery and fluid extraction if desired.

The term "transfer" as used herein shall again be construed to encompass the passage of fluid materials of any type through one or more of the internal passageways in the fluid transfer conduit 12 in either direction for any purpose. Likewise, the other embodiments listed above may be used to accomplish fluid transfer in the same manner. For example, in the multi-passageway apparatus 10 of FIG. 6 which employs a separate fluid delivery passageway 160 and fluid extraction passageway 162, fluid transfer into the apparatus 10 will be accomplished by the introduction of fluid materials through the fluid delivery passageway 160 and the withdrawal of fluid materials via the fluid extraction passageway 162. The same situation would exist in connection with the multi-conduit embodiment of FIG. 7. Accordingly, the method discussed above is applicable to all of the embodiments listed herein which are equally capable of performing effective fluid transfer in the same manner.

With continued reference to FIG. 8, use of the electrical potential transmission system 100 (which is optional but preferred) will now be discussed. In operation, the proximal end 110 and attached conductive spherical member 114 of the elongate conductive member 102/wire 104 are placed adjacent to and in direct physical contact with the round window membrane 206 (or adjacent tissue structures as previously discussed which shall be considered equivalent). As a result, electrical potentials (defined above) may be received from or transmitted to the membrane 206. Contact between the elongate conductive member 102 and the round window membrane 206 is again accomplished through appropriate physical manipulation of the apparatus 10 as previously described.

Electrical potentials may be produced in the inner ear 204 for diagnostic purposes using externally-generated tone bursts, pips, and the like in accordance with standard ECoG procedures. In situations where inner ear electrical potentials are to be analyzed, these potentials travel through the inner ear 204 to the round window membrane 206 where they are received by the conductive member 102/wire 104. The distal end 112 of the wire 104 is positioned outwardly from the ear 200 as discussed above and operatively connected to the ECoG monitoring apparatus 120. The monitoring apparatus 120 is used to record, analyze, and quantify electrical potentials received from the inner ear 204 in response to various stimuli or as an indication of resting potential activity. Further information regarding the monitoring apparatus 120 and its functional capabilities is again presented above (along with an indication that the elongate conductive member 102 may also be used in connection with standard iontophoresis procedures.) Likewise, the term "potential" as used herein shall be broadly construed to encompass any type of electrical signal, current, voltage, or impulse regardless of form, magnitude, or origin.

Finally, regarding removal of the apparatus 10 from the middle ear 202 of the patient, the insertion procedure discussed above is reversed. Removal will specifically involve deflation of the bladder member 46 which may be initiated by the reverse operation of the delivery apparatus 74 in order to transfer the inflation fluid 72 out of the internal cavity 52 of the bladder member 46, through the inflation fluid transfer passageway 34 in the conduit 12, and out of the apparatus 10 via the inflation fluid transfer conduit 64. The valve 76 (if used) may also be activated to accomplish the foregoing process (particularly if air is involved as the inflation fluid 72 which may be "bled" through the valve 76.) The bladder member 46 will then deflate, thereby allowing it to be removed from the round window niche 210 of the patient, followed by subsequent extraction of the entire apparatus 10 from the patient.

The claimed treatment systems and methods provide numerous benefits and capabilities including: (1) the creation of either a partially or completely sealed fluid-receiving zone ("fluid transfer space") within the round window niche of a patient which enables the controlled and effective delivery of therapeutic fluid compositions to the inner ear via the round window membrane; (2) the delivery of therapeutic fluid compositions to the inner ear using minimally-invasive approaches which are readily accomplished with minimum patient discomfort; (3) the transfer of a wide variety of different therapeutic agents into the middle and inner ear in a sustained, controlled, repeatable, and highly site-specific manner; (4) the removal of fluid materials from the inner ear, the round window niche, the round window membrane, and adjacent tissue regions in an efficient and thorough manner using a minimal amount of equipment and operating components; (5) the ability to electrocochleographically monitor evoked and non-evoked signals/potentials coming from the inner ear while simultaneously delivering therapeutic agents so that the effect of such agents can be immediately determined; (6) the more efficient use of iontophoretic techniques in inner ear therapy; (7) transmission into the middle and inner ear of various signals so that a diagnostic, electrophysiological analysis of internal ear structures can be made in a rapid manner; (8) the ability to readily control placement of the claimed device within the round window niche of a living subject (or other internal ear cavity) using a highly specialized, fluid-inflatable "placement control system" in the form of a bladder member; and (9) the development of a unique, multi-functional inner ear treatment and diagnostic system which enables all of the foregoing benefits to be achieved using a minimal amount of components, procedures, equipment, and technical personnel. For these reasons and the other factors listed above, the claimed invention represents a substantial advance in the art of otological treatment and diagnosis.

As a final point of information, while a preferred embodiment of the present invention involves insertion of the claimed system inside the round window niche of a living subject, the bladder member of the apparatus (and components associated therewith) can likewise be placed at least partially within any cavity or opening (natural or man-made) in the external auditory canal, middle ear, and/or inner ear (with all of these cavities/openings collectively being designated herein as "internal cavities"). As noted above, the bladder member can be inserted in an inflated or uninflated state (followed by inflation thereof). This procedure may be accomplished for the purpose of fluid delivery to the selected cavity, fluid extraction from the cavity, or selective blockage of the cavity to prevent uncontrolled fluid leakage and the like. Representative internal cavities, structures, or regions within the ear which may receive the devices listed above include but are not limited to the oval window, operculum, endolymphatic duct, the hypotympanum, and/or any bony crevice, overhang, or other region which will assist in anchoring the present invention in position. The term "internal cavity" shall also be defined to encompass any zones or regions between adjacent tissue structures (e.g. muscles, tendons, ligaments, and the like.) All of the embodiments shown in FIGS. 1–7 may be used with these and other internal cavities in the same manner previously discussed in connection with the round window niche. Accordingly, the information provided herein regarding insertion of the claimed devices within the round window niche shall be incorporated by reference relative to the use of these devices in other internal ear cavities without limitation. Likewise, it should also be understood that, in addition to the transfer of fluid materials, all embodiments of the present invention discussed herein can transfer pastes, powders, gels or other materials into the desired regions of the ear in the same manner discussed above in connection with liquid compositions. Such additional materials may require the subsequent or simultaneous addition of water or other liquids into the system to achieve proper transfer.

Having herein described preferred embodiments of the invention, it is anticipated that suitable modifications may be made thereto by individuals skilled in the art which nonetheless remain within the scope of the invention. For example, the invention shall not be limited with respect to the construction materials being employed, the fluid materials being delivered/withdrawn, and the physiological environment in which the invention is used unless otherwise indicated. The present invention shall therefore only be construed in accordance with the following claims:

The invention that is claimed is:

1. An inner ear fluid transfer and diagnostic catheter for transferring fluid materials into or out of an ear of a living subject comprising:

a fluid transfer conduit comprising a first end, a second end, and an internal passageway extending through said fluid transfer conduit from said first end to said second end, which fluid transfer conduit permits a fluid to be transferred into or out of an ear; and an inflatable bladder member connected to said fluid transfer conduit at a position thereon which does not block fluid flow through said fluid transfer conduit, said bladder member being sized for placement of at least a portion thereof within a round window niche of an ear of a subject, wherein said bladder member, when inflated, engages an internal wall of said round window niche thereby maintaining said bladder member at least partially within said round window niche.

2. The apparatus of claim 1 wherein said apparatus further comprises an elongate conductive member operatively connected to said fluid transfer conduit.

3. An inner ear fluid transfer and diagnostic catheter for transferring fluid materials into or out of an ear of a living subject comprising:

a fluid transfer conduit comprising a first end, a second end, and at least one internal passageway extending through said fluid transfer conduit from said first end to said second end, which fluid transfer conduit permits a fluid to be transferred into or out of an ear; and an inflatable annular bladder member connected to said fluid transfer conduit at a position thereon which does not block fluid flow through said fluid transfer conduit, said annular bladder member completely encircling said portion of said fluid transfer conduit and being sized for placement of at least a portion thereof within a round window niche of an ear of a subject, wherein said annular bladder member, when inflated, engages an internal side wall of said round window niche thereby forming a fluid-receiving zone between said annular bladder member and said round window membrane of said ear.

4. The apparatus of claim 3 wherein said apparatus further comprises an elongate conductive member operatively connected to said fluid transfer conduit.

5. The apparatus of claim 3, wherein said fluid-receiving zone is sealed.

6. An inner ear fluid transfer and diagnostic catheter for transferring fluid materials into or out of an ear of a living subject comprising:

a fluid transfer conduit comprising a first end, a second end, and a plurality of internal passageways extending through said fluid transfer conduit from said first end to said second end, each of said internal passageways being separate from each other within said fluid transfer conduit, which fluid transfer conduit permits a fluid to be transferred into or out of an ear; and an inflatable bladder member connected to at least a portion of said fluid transfer conduit at a position thereon which does not block fluid flow through said fluid transfer conduit, said bladder member being sized for placement of at least a portion thereof within a round window niche of an ear of a subject, wherein said bladder member, when inflated, maintains said bladder member at least partially within said round window niche, said bladder member being in fluid communication with at least one of said passageways through said fluid transfer conduit in order to allow an inflation fluid to be delivered to said bladder member through said one of said passageways so that said bladder member can be inflated.

7. The apparatus of claim 6 wherein said apparatus further comprises an elongate conductive member operatively connected to said fluid transfer conduit.

8. A medical treatment apparatus for transferring fluid materials into and out of the inner ear of a living subject through the round window niche and the round window membrane of said subject comprising:

a fluid transfer conduit comprising a first end, a second end, at least one internal passageway extending through said fluid transfer conduit from said first end to said second end, and a semi-permeable membrane operatively attached to said fluid transfer conduit at a position which will enable said membrane to at least partially block said passageway so that said fluid materials to be transferred through said passageway will first need to pass through said membrane; and an inflatable bladder member operatively connected to at least a portion of said fluid transfer conduit at a position thereon which allows said fluid materials to pass into and out of said apparatus, said bladder member being sized for placement within said round window niche of said subject, said round window niche comprising an internal side wall therein which is engaged by said bladder member when said bladder member is inflated in order to maintain said bladder member at least partially within said round window niche.

9. The apparatus of claim 8 wherein said apparatus further comprises an elongate conductive member operatively connected to said fluid transfer conduit.

10. An inner ear fluid transfer and diagnostic catheter for transferring materials into or out of an ear of a living subject comprising:

a fluid transfer conduit comprising a first end, a second end, and at least one internal passageway extending through said fluid transfer conduit from said first end to said second end, which fluid transfer conduit permits a fluid to be transferred into or out of an ear; and an inflatable bladder member connected to at least a portion of said fluid transfer conduit at a position thereon which does not block fluid flow through said fluid transfer conduit, said bladder member being sized for placement of at least a portion thereof within at least one internal cavity in an ear of a subject, said bladder member being engaged within said internal cavity when said bladder member is inflated in order to maintain said bladder member at least partially within said internal cavity.

11. The apparatus of claim 10 wherein said apparatus further comprises an elongate conductive member operatively connected to said fluid transfer conduit.

12. A method for moving fluid materials through the round window niche and the round window membrane in the ear of a living subject, said method comprising:

inserting the apparatus of claim 1 into an ear of a subject such that said bladder member is positioned at least partially into a round window niche of an ear of said subject;

inflating said bladder member so that said bladder member engages an internal side wall of said round window niche, thereby maintaining said bladder member at least partially within said round window niche; and transferring fluid materials through said fluid transfer conduit of said apparatus.

13. The method of claim 12 further comprising:

providing an elongate conductive member operatively connected to said fluid transfer conduit; and placing at least a portion of said elongate conductive member in direct contact with an internal ear component selected from the group consisting of a round window membrane and at least one ear tissue structure adjacent to a round window membrane.

14. A method for moving fluid materials through the round window niche and the round window membrane in the ear of a living subject, said method comprising:

inserting the apparatus of claim 3 into an ear of a subject such that said annular bladder member at least partially into a round window niche of said subject;

inflating said annular bladder member so that said bladder member engages said internal side wall of said round window niche, thereby maintaining said bladder member at least partially within said round window niche and to likewise create a fluid-receiving zone between said annular bladder member and said round window membrane; and transferring fluid materials through said fluid transfer conduit of said apparatus.

15. The method of claim 14 further comprising:

providing an elongate conductive member operatively connected to said fluid transfer conduit; and placing at least a portion of said elongate conductive member in direct contact with an internal ear component selected from the group consisting of a round window membrane and at least one ear tissue structure adjacent to a round window membrane.

16. The method of claim 14, wherein the fluid-receiving zoned is sealed.

17. A method for moving fluid materials through the round window niche and the round window membrane in the ear of a living subject, said method comprising the steps of:

inflating said bladder member of the apparatus of claim 1;

inserting said bladder member at least partially into a round window niche of a subject after said inflating of said bladder member, said bladder member engaging said internal side wall of said round window niche in order to maintain said bladder member at least partially within said round window niche; and transferring fluid materials through said fluid transfer conduit.

18. A method for moving fluid materials through an internal cavity within an ear of a living subject, said method comprising:

inserting the apparatus of claim 20 into an ear of a subject such that said bladder member is positioned at least partially into an internal cavity in said ear of said subject; and inflating said bladder member so that said bladder member is at least partially engaged and maintained within said internal cavity.

19. A method for moving fluid materials through an internal cavity within an ear of a living subject, said method comprising:

inflating the bladder member of the apparatus of claim 20; and inserting said bladder member at least partially into an internal cavity in an ear of a subject after said inflating of said bladder member so that said bladder member is at least partially engaged and maintained within said internal cavity.

20. An inner ear fluid transfer and diagnostic catheter for transferring fluid materials into or out of an ear of a living subject comprising:

(a) a fluid transfer conduit comprising a first end, a second end, and an internal passageway extending through said fluid transfer conduit from said first end to said second end, which fluid transfer conduit permits a fluid to be transferred into or out of an ear; and (b) an inflatable bladder member connected to said fluid transfer conduit at a position thereon which does not block fluid flow through said fluid transfer conduit, said bladder member being sized for placement of at least a portion thereof within an internal cavity of an ear of a subject, wherein said bladder member, when inflated, engages an internal wall of said internal cavity, thereby maintaining said bladder member at least partially within said internal cavity.

* * * * *